US010321819B2

(12) United States Patent
Ishiai et al.

(10) Patent No.: US 10,321,819 B2
(45) Date of Patent: Jun. 18, 2019

(54) OPHTHALMIC IMAGING APPARATUS

(71) Applicant: KABUSHIKI KAISHA TOPCON, Itabashi-ku (JP)

(72) Inventors: Ryota Ishiai, Kita-ku (JP); Masaki Nakano, Soka (JP)

(73) Assignee: KABUSHIKI KAISHA TOPCON, Tokyo (JP)

(*) Notice: Subject to any disclaimer, the term of this patent is extended or adjusted under 35 U.S.C. 154(b) by 75 days.

(21) Appl. No.: 15/524,096

(22) PCT Filed: Jul. 13, 2015

(86) PCT No.: PCT/JP2015/070010
§ 371 (c)(1),
(2) Date: May 3, 2017

(87) PCT Pub. No.: WO2016/084419
PCT Pub. Date: Jun. 2, 2016

(65) Prior Publication Data
US 2017/0325679 A1    Nov. 16, 2017

(30) Foreign Application Priority Data
Nov. 25, 2014 (JP) ................. 2014-237932

(51) Int. Cl.
A61B 3/12 (2006.01)
A61B 3/00 (2006.01)
(Continued)

(52) U.S. Cl.
CPC ............ A61B 3/102 (2013.01); A61B 3/0041 (2013.01); A61B 3/0058 (2013.01); A61B 3/12 (2013.01); A61B 3/14 (2013.01); A61B 3/1225 (2013.01)

(58) Field of Classification Search
CPC ..... A61B 3/102; A61B 3/0041; A61B 3/0058; A61B 3/12; A61B 3/14
(Continued)

(56) References Cited

FOREIGN PATENT DOCUMENTS

| JP | 2014-113385 A | 6/2014 |
| JP | 2014/140489 A | 8/2014 |

(Continued)

OTHER PUBLICATIONS

International Search Report dated Oct. 13, 2015 in PCT/JP2015/070010 filed Jul. 13, 2015.
(Continued)

Primary Examiner — James R Greece
(74) Attorney, Agent, or Firm — Xsensus LLP

(57) ABSTRACT

An ophthalmic imaging apparatus of an embodiment scans a subject's eye with OCT to acquire a cross sectional image. A measurement unit performs OCT. An imaging unit acquires a moving image of the subject's eye. A display controller controls a display device to display the moving image acquired by the imaging unit, and two or more scan pattern images corresponding to two or more scan lines representing scan positions and scan directions in the moving image and arranged such that at least two of the two or more scan pattern images intersect one another. An operation unit is used for changing a relative position between the two or more scan pattern images. A measurement controller controls the measurement unit to perform OCT based on the two or more scan lines corresponding to the two or more scan pattern images after the relative position have been changed.

22 Claims, 14 Drawing Sheets

(51) Int. Cl.
*A61B 3/10* (2006.01)
*A61B 3/14* (2006.01)

(58) Field of Classification Search
USPC .................................... 351/205–206, 246
See application file for complete search history.

(56) References Cited

FOREIGN PATENT DOCUMENTS

| | | |
|---|---|---|
| JP | 2014-147505 A | 8/2014 |
| JP | 2014/155875 A | 8/2014 |
| JP | 2014140489 A2 * | 8/2014 |

OTHER PUBLICATIONS

Office Action received in Japanese Patent Application No. 2014-237932, dated Nov. 20, 2018 with English translation.

* cited by examiner

OPHTHALMIC IMAGING APPARATUS

FIELD

Embodiments described herein relate generally to an ophthalmic imaging apparatus.

BACKGROUND

In the field of ophthalmology, various kinds of apparatuses are used for imaging a subject's eye. In recent years, optical coherence tomography apparatuses capable of acquiring cross sectional images and three dimensional images of a fundus and of an anterior segment have been attracting attention.

In the optical coherence tomography apparatuses, various scan patterns are used according to the objects to be imaged, the targets of analysis, or the like. Examples of scan patterns include line scan (e.g., horizontal scan, vertical scan, etc.), cross scan, radial scan, concentric scan, three dimensional scan, and the like.

Furthermore, a scan patterns that is a combination of two or more scan patterns can also be employed. For example, there is a scan pattern (referred to as multi-line cross scan) in which a group of horizontal scan lines parallel to each other and a group of vertical scan lines parallel to each other are placed so as to be perpendicular to each other in the vicinity of the center positions of the both groups of scan lines. In practice, a scan pattern called five line cross scan is applied which is a combination of five horizontal scan lines and five vertical scan lines.

A user sets a scan position as well as selecting a scan pattern. For example, the user selects a five line cross scan as a scan pattern and sets a scan position such that an intersection area of the five line cross scan is placed at a site of interest (e.g., macula or the like) of the subject's eye. The setting of the scanning position is performed by moving a mark (i.e., image) representing a scan pattern displayed on an observation image (i.e., moving image) of the subject's eye.

[Patent Document 1] Japanese Unexamined Patent Application Publication No. 2014-155875

With the conventional ophthalmic imaging apparatus, as described above, in order to observe the site of interest and peripheral sites thereof, the scan pattern (i.e., the mark) is moved while maintaining the shape of the selected scan pattern.

However, with the conventional ophthalmic imaging apparatus, the scan pattern can be moved only within a scannable area, which is limited by hardware constraints or the like, and thus it is sometimes impossible to place the intersection area of the scan patterns at a desired position within the scannable area. For example, when it is desired to observe a site of interest located in the vicinity of the boundary of the scannable area and peripheral sites of the site of interest, it is impossible to set the scan position at the site of interest or in the vicinity thereof and thus to observe the site of interest. In this case, the site of interest is required to move in the observation image by moving a fixation target or the like, and the degree of freedom of scanning decreases.

SUMMARY

The present invention is made to solve the aforementioned problem, and the object thereof is to provide a technology for increasing the degree of freedom of scanning.

An ophthalmic imaging apparatus of an embodiment scans a subject's eye with optical coherence tomography to acquire a cross sectional image. The ophthalmic imaging apparatus includes a measurement unit, an imaging unit, a display controller, an operation unit, and a measurement controller. The measurement unit performs optical coherence tomography. The imaging unit acquires a moving image of the subject's eye. The display controller controls a display device to display the moving image acquired by the imaging unit, and two or more scan pattern images corresponding to two or more scan lines representing scan positions and scan directions in the moving image and arranged such that at least two of the two or more scan pattern images intersect one another. The operation unit is used for changing a relative position between the two or more scan pattern images. The measurement controller controls the measurement unit to perform optical coherence tomography based on the two or more scan lines corresponding to the two or more scan pattern images after the relative position have been changed.

According to the present embodiments, the degree of freedom of scanning can be increased.

DETAILED DESCRIPTION

Figure 1:
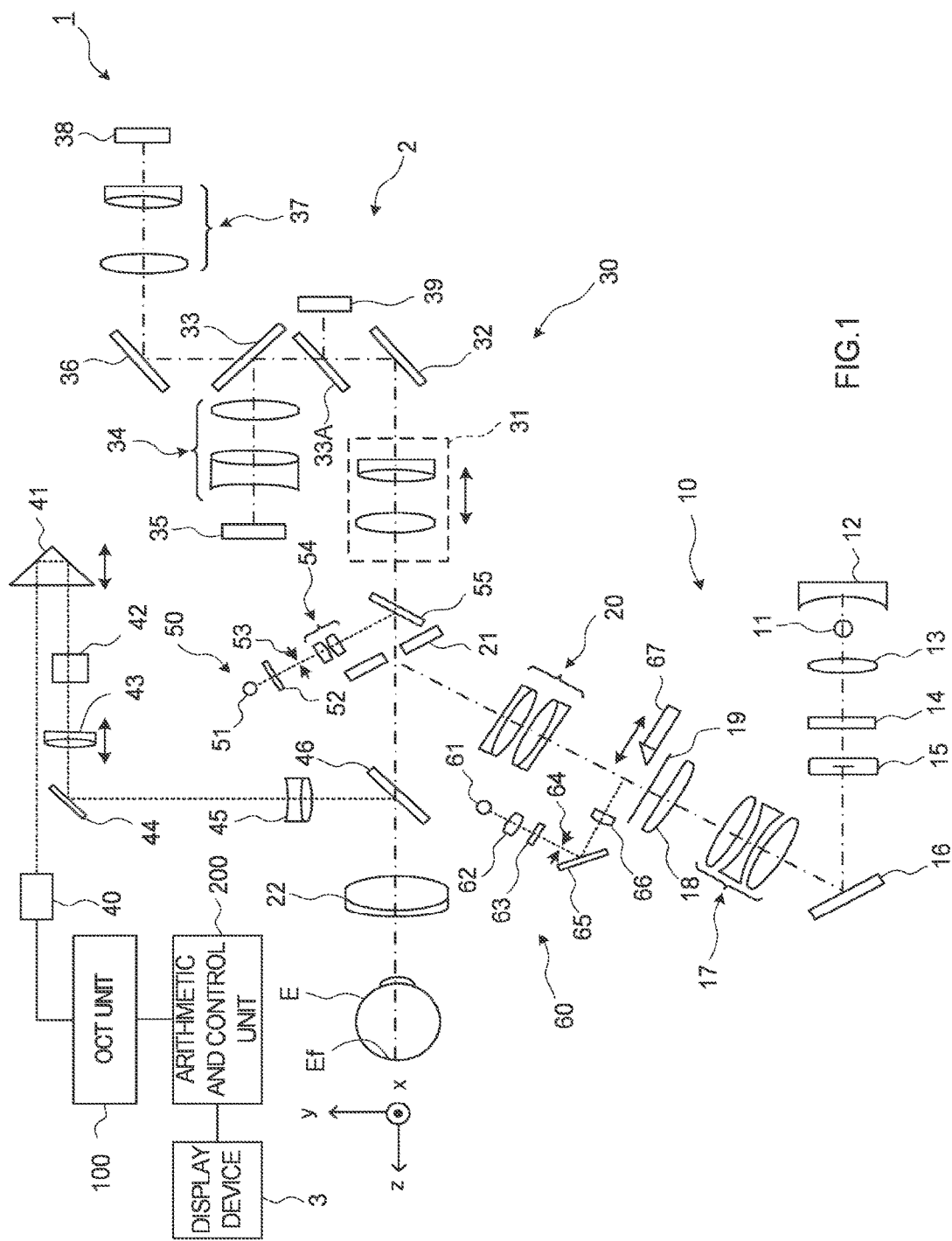
FIG. 1 is a schematic diagram illustrating an example of the configuration of an ophthalmic imaging apparatus according to an embodiment.

Exemplary embodiments of the present invention will be described in detail with referring to the drawings. An ophthalmic imaging apparatus according to the present embodiment has a function of an optical coherence tomography apparatus and performs optical coherence tomography (hereinafter referred to as OCT) of a subject's eye. The OCT is performed on an arbitrary site of the subject's eye, for example, on the fundus or on the anterior segment.

In this specification, images acquired using OCT may be collectively referred to as "OCT images". In addition, the contents of the documents cited in the specification can be incorporated as contents of the following embodiments.

The following embodiment describes an ophthalmic imaging apparatus capable of performing Fourier domain OCT. For example, the ophthalmic imaging apparatus according to the embodiment may be configured to perform swept source OCT. It should be noted that the configuration according to the present embodiment can also be applied to an ophthalmic imaging apparatus capable of performing OCT of other type than the swept source OCT such as spectral domain OCT. Although the embodiment describes a multifunctional apparatus including an OCT apparatus and a fundus camera, the configuration for OCT described in the embodiment may be combined with any other type of ophthalmic imaging apparatus than the fundus camera, such as a scanning laser ophthalmoscope (SLO), a slit lamp microscope, an ophthalmic surgical microscope, a photocoagulator. Alternatively, the configuration of the embodiment may be applied to an (single functional) OCT apparatus.

[Configuration]

As shown in FIG. 1, the ophthalmic imaging apparatus 1 includes a fundus camera unit 2, an OCT unit 100, and an arithmetic and control unit 200. The fundus camera unit 2 has substantially the same optical system as the conventional fundus camera. The OCT unit 100 is provided with an optical system for performing OCT. The arithmetic and control unit 200 is provided with a computer for performing various arithmetic processes and control processes.

[Fundus Camera Unit]

As illustrated in FIG. 1, the fundus camera unit 2 is provided with an optical system for acquiring two dimensional images (fundus images) rendering the surface morphology of a fundus Ef of a subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 projects illumination light onto the fundus Ef. The imaging optical system 30 guides the illumination light reflected from the fundus Ef to imaging devices (CCD image sensors 35 and 38). Each of the CCD image sensors 35 and 38 is sometimes simply referred to as a "CCD". Further, the imaging optical system 30 guides measurement light coming from the OCT unit 100 to the subject's eye E, and guides the measurement light returning from the subject's eye E to the OCT unit 100.

An observation light source 11 of the illumination optical system 10 includes, for example, a halogen lamp or a light emitting diode (LED). The light (observation illumination light) output from the observation light source 11 is reflected by a reflection mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding area of an aperture part) of an aperture mirror 21, penetrates a dichroic mirror 46, and refracted by an objective lens 22, thereby illuminating the fundus Ef.

The observation illumination light reflected from the fundus is refracted by the objective lens 22, penetrates the dichroic mirror 46, passes through the aperture part formed in the center area of the aperture mirror 21, passes through a dichroic mirror 55, travels through a focusing lens 31, and is reflected by a mirror 32. Further, the fundus reflection light passes through a half mirror 33A, is reflected by a dichroic mirror 33, and forms an image on the light receiving surface of the CCD image sensor 35 by a condenser lens 34. The CCD image sensor 35 detects, for example, the fundus reflection light at a predetermined frame rate. An image (observation image) based on the fundus reflection light detected by the CCD image sensor 35 is displayed on a display device 3. Note that when the imaging optical system 30 is focused on the anterior segment, an observation image of the anterior segment of the subject's eye E is displayed.

The imaging light source 15 is formed of, for example, a xenon lamp or an LED. The light (imaging illumination light) output from the imaging light source 15 is projected onto the fundus Ef via the same route as that of the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source.

A liquid crystal display (LCD) 39 displays a fixation target or a visual target for measuring visual acuity. The fixation target is an indicator for fixating the subject's eye E, and is used when performing fundus photography and OCT measurement.

Part of the light output from the LCD 39 is reflected by the half mirror 33A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position of the subject's eye E include, as with conventional fundus cameras, a position for acquiring an image centered on the macula of the fundus Ef, a position for acquiring an image centered on the optic nerve head, a position for acquiring an image centered on the fundus center between the macula and the optic nerve head, and the like. Further, the display position of the fixation target may be arbitrarily changed.

Further, as with conventional fundus cameras, the fundus camera unit 2 is provided with an alignment optical system 50 and a focus optical system 60. The alignment optical system 50 generates an indicator (referred to as an alignment indicator) for the position matching (i.e., the alignment) of the optical system with respect to the subject's eye E. The focus optical system 60 generates an indicator (referred to as a split indicator) for adjusting the focus with respect to the subject's eye E.

The light (alignment light) output from an LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E by the objective lens 22.

The alignment light reflected from the cornea travels through the objective lens 22, the dichroic mirror 46 and the above-mentioned aperture part. Part of the cornea reflection light penetrates the dichroic mirror 55, passes through the focusing lens 31, is reflected by the mirror 32, penetrates the half mirror 33A, is reflected by the dichroic mirror 33, and is projected onto the light receiving surface of the CCD image sensor 35 by the condenser lens 34. The display device 3 displays the received image (alignment indicator) captured by the CCD image sensor 35 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

To conduct focus adjustment, the reflective surface of a reflection rod 67 is arranged in a slanted position on the optical path of the illumination optical system 10. The light (focus light) output from an LED 61 of the focus optical system 60 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus passes through the same route as the alignment light reflected from the cornea and is detected by the CCD image sensor 35. The display device 3 displays the received image (split indicator) captured by the CCD image sensor 35 together with an observation image. As in the conventional case, the arithmetic and control unit 200 analyzes the position of the split indicator, and moves the focusing lens 31 and the focus optical system 60 for focusing (automatic focusing). The user may perform the focusing manually while visually checking the split indicator.

The dichroic mirror 46 branches an optical path for OCT from an optical path for fundus photography. The dichroic mirror 46 reflects light of wavelengths used in OCT, and transmits light for fundus photography. This optical path for OCT is provided with, in order from the OCT unit 100 side, a collimator lens unit 40, an optical path length changing unit 41, a variable cross cylinder lens (hereinafter referred to as VCC lens) 47, an optical scanner 42, a focusing lens 43, a mirror 44, and a relay lens 45.

The optical path length changing unit 41 is movable in directions indicated by the arrow in FIG. 1, thereby changing the length of the optical path for OCT measurement. This change in the optical path length is used for correcting the optical path length according to the axial length of the subject's eye E, adjusting the interference state, and the like. The optical path length changing unit 41 includes, for example, a corner cube and a mechanism for moving it.

The optical scanner 42 is disposed at a position optically conjugate with the pupil of the subject's eye E. The optical scanner 42 changes the traveling direction of the light (measurement light LS) passing through the OCT optical path. Thereby, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism that independently drives the galvano mirrors. Thereby, it is possible to scan the measurement light LS in an arbitrary direction in the xy plane.

[OCT Unit]

Figure 2:
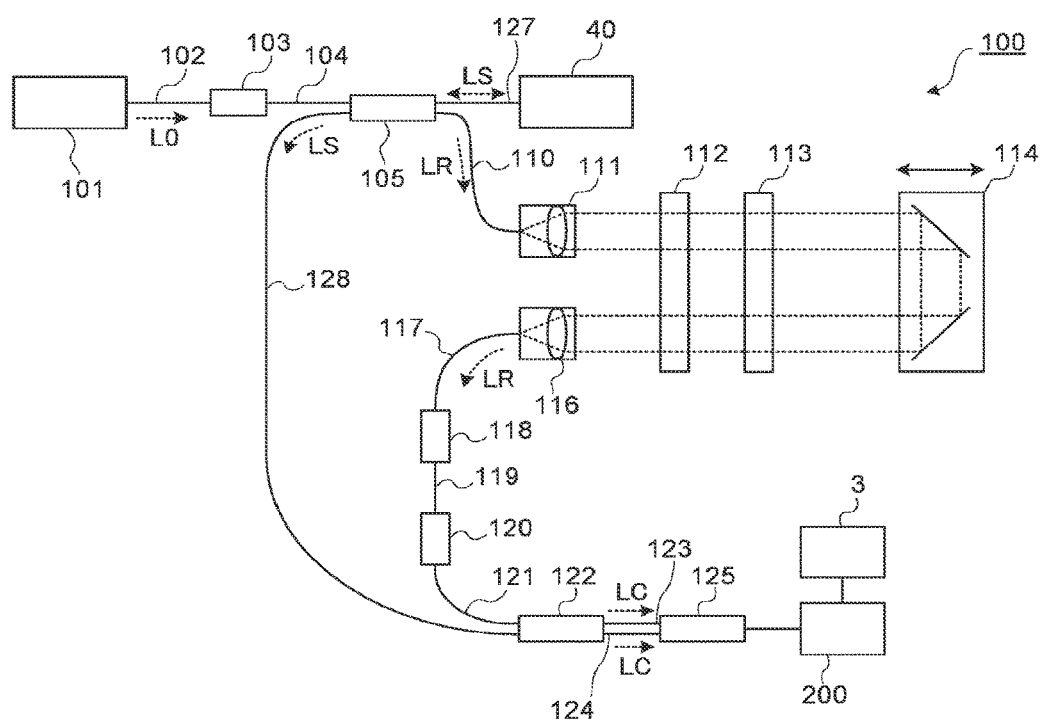
FIG. 2 is a schematic diagram illustrating an example of the configuration of the ophthalmic imaging apparatus according to the embodiment.

Exemplary configuration of the OCT unit 100 is shown in FIG. 2. The OCT unit 100 includes an optical system for acquiring OCT images of the subject's eye E. The optical system has the same configuration as with the conventional swept source OCT apparatus. More specifically, the optical system is an interference optical system that splits the light from the wavelength scanning type (wavelength tunable type) light source into the measurement light and the reference light, make the measurement light returning from the subject's eye E and the reference light having traveled through the reference optical path interfere with each other to generate interference light, and to detect the interference light. The detection result (detection signal) of the interference light obtained by the interference optical system is a signal indicating a spectrum of the interference light, and is sent to the arithmetic and control unit 200.

Like the general swept source OCT apparatus, a light source unit 101 includes a wavelength scanning type (wavelength tunable type) light source capable of scanning (sweeping) the wavelengths of emitted light. The light source unit 101 temporally changes the output wavelengths within the near infrared wavelength bands that cannot be visually recognized with human eyes.

The light L0 output from the light source unit 101 is guided to a polarization controller 103 through an optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to a fiber coupler 105 through an optical fiber 104 and is split into the measurement light LS and the reference light LR.

The reference light LR is guided to a collimator 111 through an optical fiber 110 and becomes a parallel light beam. The reference light LR, which has become a parallel light beam, is guided to a corner cube 114 via an optical path length correction member 112 and a dispersion compensation member 113. The optical path length correction member 112 functions as a delay means to match the optical path length (optical distance) of the reference light LR and the optical path length of the measurement light LS. The dispersion compensating member 113 functions as a dispersion compensating means to match the dispersion characteristics of the reference light LR and the measurement light LS.

The corner cube 114 changes the traveling direction of the reference light LR that has become a parallel light beam by the collimator 111 in the opposite direction. The optical path of the reference light LR incident on the corner cube 114 and the optical path of the reference light LR emitted from the corner cube 114 are parallel. Further, the corner cube 114 is movable in a direction along the incident light path and the emitting light path of the reference light LR. Through this movement, the length of the optical path of the reference light LR is changed.

The configuration shown in FIG. 1 and FIG. 2 include both the optical path length changing unit 41 that changes the length of the optical path (measurement optical path, measurement arm) of the measurement light LS and the corner cube 114 that changes the length of the optical path (reference optical path, reference arm) of the reference light LR. However, the ophthalmic imaging apparatus may include any one of the optical path length changing unit 41 and the corner cube 114. The ophthalmic imaging apparatus can also change the difference between the measurement optical path length and the reference optical path length by using other optical members.

The reference light LR that has traveled through the corner cube 114 travels through the dispersion compensating member 113 and the optical path length correction member 112 and is converted from the parallel light beam to the convergent light beam by a collimator 116 and enters an optical fiber 117 to be guided to a polarization controller 118. Thereby, the polarization state of the reference light LR is adjusted.

The polarization controller 118 has the same configuration as, for example, the polarization controller 103. The reference light LR whose polarization state has been adjusted by the polarization controller 118 is guided to an attenuator 120 through an optical fiber 119 and the light amount is adjusted under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into a parallel light beam reaches the dichroic mirror 46 via the optical path length changing unit 41, the optical scanner 42, the focusing lens 43, the mirror 44, and the relay lens 45. Then, the measurement light LS is reflected by the dichroic mirror 46, refracted by the objective lens 22, and irradiated onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 are guided to a detector 125 through optical fibers 123 and 124, respectively.

The detector 125 is, for example, a balanced photo diode that has a pair of photodetectors for respectively detecting the pair of the interference light LC and outputs a difference between the pair of detection results obtained by the pair of photodetectors. The detector 125 sends the detection result (i.e., detection signal) to the arithmetic and control unit 200. For example, the arithmetic and control unit 200 performs a Fourier transform or the like on the spectral distribution based on the detection result obtained by the detector 125 for each series of wavelength scans (for each A line), thereby forming reflection intensity profiles in each A line. In addition, the arithmetic and control unit 200 forms image data by applying imaging processing to the reflection intensity profiles of the respective A lines.

The present embodiment employs an interference optical system of Michelson type is employed, but an interference optical system of any type, such as Mach-Zehnder type, can be employed.

[Arithmetic and Control Unit]

The configuration of the arithmetic and control unit 200 will be described. The arithmetic and control unit 200 analyzes a detection signal input from the detector 125 to form an OCT image of the subject's eye E. The arithmetic processing for that purpose is the same as the conventional swept source OCT apparatus.

Further, the arithmetic and control unit 200 controls each part of the fundus camera unit 2, the display device 3, and the OCT unit 100. For example, the arithmetic and control unit 200 controls the display device 3 to display the OCT image of the subject's eye E.

Also, as the control of the retinal camera unit 2, the arithmetic and control unit 200 perform following controls: the operation control of the observation light source 11, of the imaging light source 15 and of the LEDs 51 and 61; the operation control of the LCD 39; the movement control of the focusing lenses 31 and 43; the movement control of the reflection rod 67; the movement control of the focus optical system 60; the movement control of the optical path length changing unit 41; the operation control of the optical scanner 42, and the like.

Further, as the control of the OCT unit 100, the arithmetic and control unit 200 perform following controls: the operation control of the light source unit 101; the movement control of the corner cube 114; the operation control of the detector 125; the operation control of the attenuator 120; the operation controls of the polarization controllers 103 and 118, and the like.

Like conventional computers, the arithmetic and control unit 200 includes a microprocessor, a random access memory (RAM), a read only memory (ROM), a hard disk drive, a communication interface, and the like. A storage device such as the hard disk drive stores a computer program for controlling the ophthalmic imaging apparatus 1. The arithmetic and control unit 200 may include various kinds of circuit boards such as circuit boards for forming OCT images. In addition, the arithmetic and control unit 200 may include an operation device (input device) such as a keyboard and a mouse, and a display device such as an LCD.

The fundus camera unit 2, the display device 3, the OCT unit 100, and the arithmetic and control unit 200 may be integrally configured (that is, configured within a single housing). Alternatively, they may be placed in two or more housings in a distributed fashion.

[Control System]

Figure 3:
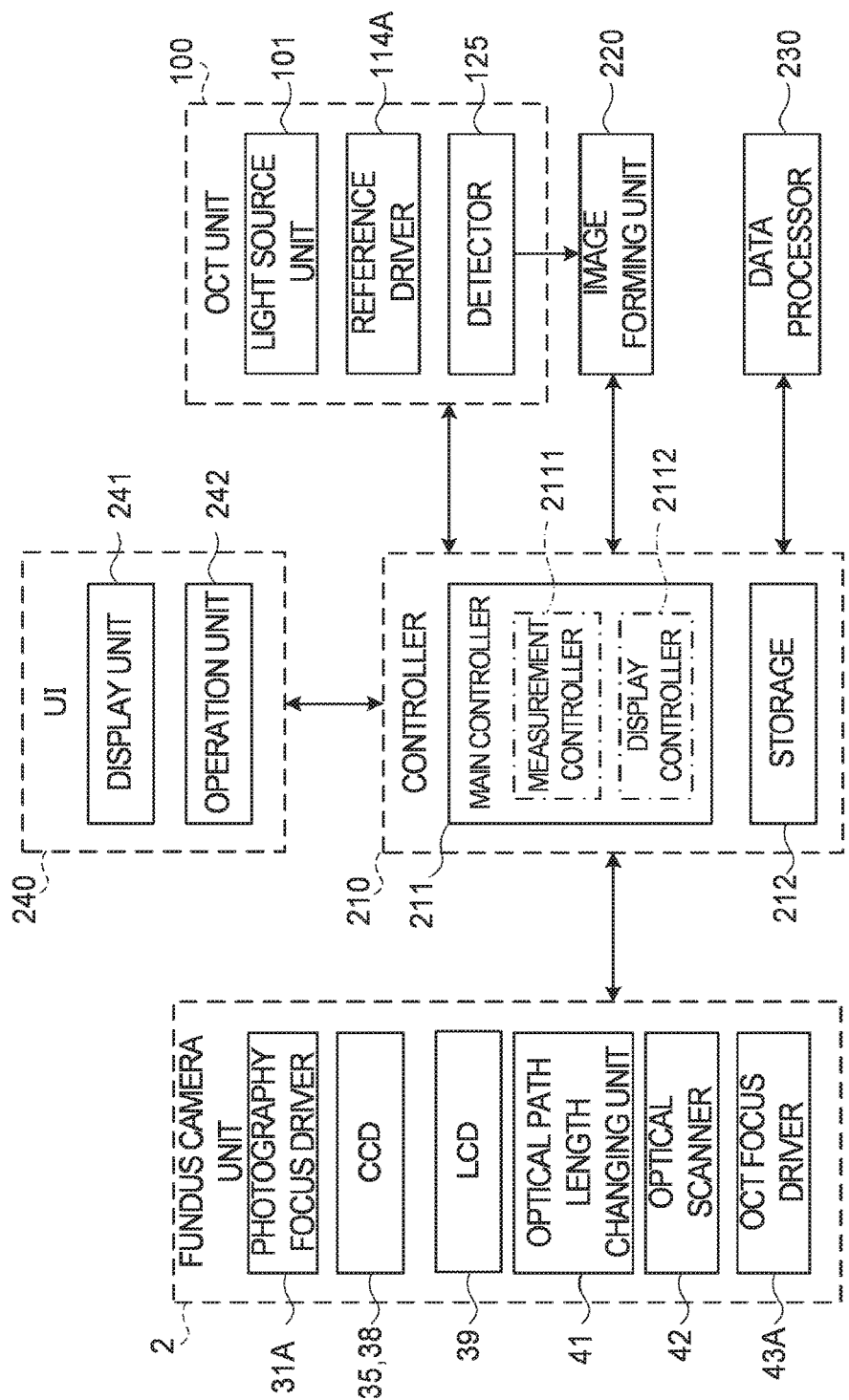
FIG. 3 is a schematic diagram illustrating an example of the configuration of the ophthalmic imaging apparatus according to the embodiment.

The configuration of the control system of the ophthalmic imaging apparatus 1 will be described with referring to FIG. 3. In FIG. 3, some components of the ophthalmic imaging apparatus 1 are omitted, and particularly necessary components are selectively shown for describing the present embodiment.

(Controller)

The control system of the fundus observation apparatus 1 is centered around a controller 210. The controller 210 includes, for example, the microprocessor, RAM, ROM, a hard disk drive, and a communication interface. The controller 210 is provided with a main controller 211 and a storage unit 212.

(Main Controller)

The main controller 211 performs various types of controls mentioned above. In particular, as shown in FIG. 3, the main controller 211 controls a photography focus driver 31A of the fundus camera unit 2, the CCD image sensors 35 and 38, the LCD 39, the optical path length changing unit 41, the optical scanner 42, and an OCT focus driver 43A, and the light source unit 101 of, a reference driver 114A of, the detector 125 of, and the like of the OCT unit 100.

The photography focus driver 31A moves the focusing lens 31 in the optical axis direction. With this, the focus position of the imaging optical system 30 is changed. Incidentally, the main controller 211 may control an optical system driver (not illustrated) to three dimensionally moves the optical system of the fundus camera unit 2. This control is used in alignment and tracking. Here, tracking is to move the optical system of the apparatus according to the movement of the subject's eye E. To perform tracking, alignment and focusing are performed in advance. The tracking is performed by moving the optical system of the apparatus in real time according to the position and orientation of the subject's eye E based on the moving image obtained by imaging the eye E, thereby maintaining a suitable positional relationship in which alignment and focusing are adjusted.

The OCT focus driver 43A moves the focusing lens 43 along the optical axis of the measurement optical path. Thereby, the focal position of the measurement light LS is changed. The focal position of the measurement light LS corresponds to the depth position (i.e., z position) of the beam waist of the measurement light LS.

The reference driver 114 A moves the corner cube 114 provided in the reference optical path. Thereby, the length of the reference light path is changed. As described above, the ophthalmic imaging apparatus 1 may include any one of the optical path length changing unit 41, and the corner cube 114 and the reference driver 114A.

As shown in FIG. 3, the main controller 211 includes a measurement controller 2111 and a display controller 2112.

(Measurement Controller)

The measurement controller 2111 controls the fundus camera unit 2 and the OCT unit 100 to perform OCT measurement. For example, the measurement controller 2111 controls the following conditions: a condition related to scanning of the measurement light LS (referred to as scan conditions); a condition related to focus of the measurement light LS (referred to as focus conditions); a condition related to the interference state between the measurement light LS and the reference light LR (referred to as interference conditions); a condition related to fixation (referred to as fixation conditions), and the like. The scan conditions include a scan pattern, a scan interval, a scannable area, and the like, which are related to the control of the optical scanner 42. Further, the scan conditions include the selection of a scan pattern, the scan position and/or the scan direction of the selected scan pattern, the shape of the scan pattern, and the like. The scan pattern is a condition representing the shape of the scan, and specific examples thereof include a line scan with the shape of a line segment, a circle scan with the shape of a circle, a raster scan, a cross scan, a radial scan, and the like. The scan interval includes the interval between adjacent scan patterns, the interval between scan areas to be described later. For multi-line cross scans, the scan interval includes the interval between adjacent scan lines in the scan pattern. The scannable area is uniquely determined according to the hardware configuration of the ophthalmic imaging apparatus 1 or the like. The position of the scannable area can be controlled. The focus conditions include the focal position of the measurement light LS related to the control of the focusing lens 43 (i.e., the control of the OCT focus driver 43A) and the like. The interference conditions are related to the control of the focusing lens 43 (i.e., the OCT focus driver 43A), the control of the corner cube 114 (the reference driver 114A), the control of the polarization controller 118, the control of the attenuator 120, and the like. The fixation conditions include the projection position of the fixation target related to the control of the LCD 39. The measurement controller 2111 performs control based on the conditions having been set. Note that the conditions controlled by the measurement controller 2111 are not limited to those described here. For example, the conditions controlled by the measurement controller 2111 may include the dioptric correction in accordance with the diopter of the subject's eye E.

(Display Controller)

The display controller 2112 displays various kinds of information on a display unit 241. The display controller 2112 can superimpose the scan pattern image on the observation image (moving image) of the subject's eye E, and display the scan pattern image and the observation image on the display unit 241. The scan pattern image corresponds to the scan pattern controlled by the measurement controller 2111. The observation image (moving image) of the subject's eye E is generated based on the fundus reflection light detected by the CCD image sensor 35 (or the CCD image sensor 38).

(Storage Unit)

The storage 212 stores various types of data. Examples of the data stored in the storage 212 include, for example, image data of an OCT image, image data of a fundus image, and subject's eye information. The subject's eye information includes information related to a subject such as patient ID and name, information related to the subject's eye such as identification information of left eye/right eye, and the like. In addition, the storage 212 stores various types of programs and data to run the ophthalmic imaging apparatus 1.

(Image Forming Unit)

An image forming unit 220 forms image data of a tomographic image of the fundus Ef based on a detection signal from the detector 125. That is, the image forming unit 220 forms the image data of the subject's eye E based on a detection result of the interference light LC obtained by the interference optical system. As in the conventional spectral domain OCT, the image formation process includes noise removal (noise reduction), filtering, fast Fourier transform (FFT), and the like. The image data acquired in this manner is a data set including a group of image data formed by imaging the reflection intensity profiles of a plurality of A lines. Here, the A lines are the paths of the measurement light LS in the eye E.

In order to improve the image quality, it is possible to repeatedly perform scan with the same pattern a plurality of times to collect a plurality of data sets, and to compose (i.e., average) the plurality of data sets.

The image forming unit 220 includes, for example, the aforementioned circuit boards. Incidentally, "image data" and an "image" based thereon may be treated in the same way in this specification. Further, a site of the subject's eye E and an image thereof may also be treated in the same way.

(Data Processor)

The data processor 230 performs various types of data processing (e.g., image processing) and various types of analysis on an OCT image formed by the image forming unit 220. For example, the data processor 230 performs various correction processes such as brightness correction and dispersion correction of images. The data processor 230 performs various types of image processing and analysis on images (fundus image, anterior segment image, etc.) captured by the fundus camera unit 2.

The data processor 230 can form volume data (voxel data) of the subject's eye E by performing known image processing such as interpolation processing for interpolating pixels between cross sectional images. In the case of displaying an image based on the volume data, the data processor 230 performs a rendering process on the volume data so as to form a pseudo three dimensional image viewed from a specific line-of-sight direction.

The data processor 230 can perform registration (i.e., position matching) between a fundus image and an OCT image. When the fundus image and the OCT image are obtained in parallel, the registration between the fundus image and the OCT image, which have been (almost) simultaneously obtained, can be performed using the optical axis of the imaging optical system 30 as a reference. Such registration can be achieved since the optical system for the fundus image and that for the OCT image are coaxial. Besides, regardless of the timing of obtaining the fundus image and that of the OCT image, the registration between the fundus image and the OCT image can be achieved by performing the registration between the fundus image with a front image formed by projecting at least part of the image area in the OCT image corresponding to the fundus Ef onto the xy plane. This registration method can also be employed when the optical system for acquiring fundus image and the optical system for OCT are not coaxial. Further, when both the optical systems are not coaxial, if the relative positional relationship between these optical systems is known, the registration can be performed with referring to the relative positional relationship in a manner similar to the case of coaxial optical systems.

The data processor 230 that functions as above includes, for example, a microprocessor, RAM, ROM, a hard disk drive, a circuit board, and the like. The storage device such as a hard disk drive stores, in advance, computer programs for causing the microprocessor to implement the above functions.

(User Interface)

A user interface 240 includes the display unit 241 and an operation unit 242. The display unit 241 includes the aforementioned display device of the arithmetic and control unit 200 and the display device 3. The operation unit 242 includes the aforementioned operation device of the arithmetic and control unit 200. The operation unit 242 may include various kinds of buttons and keys provided on the housing of the ophthalmic imaging apparatus 1, or provided outside the ophthalmic imaging apparatus 1. Further, the display unit 241 may include various kinds of display devices, such as a touch panel placed on the housing of the fundus camera unit 2.

Note that the display unit 241 and the operation unit 242 need not necessarily be formed as separate devices. For example, a device like a touch panel, which has a display function integrated with an operation function, can be used. In such a case, the operation unit 242 includes the touch panel and a computer program. The content of an operation performed using the operation unit 242 is fed to the controller 210 as an electrical signal. Moreover, operations and inputs of information may be performed using a graphical user interface (GUI) displayed on the display unit 241 and the operation unit 242.

The ophthalmic imaging apparatus 1 is configured to be capable of storing a scan pattern applied to the OCT measurement and applying the stored scan pattern to the subsequent OCT measurement thereafter. In this case, for example, the operation unit 242 is used to input identification information of the subject. The storage unit 212 stores operation information including scan information representing the scan pattern applied to the subject's eye E in association with the identification information. When identification information is newly input using the operation unit 242, the measurement controller 2111 retrieves the scan information associated with the newly input identification information from the storage unit 212. The measurement controller 2111 controls the fundus camera unit 2 and the OCT unit 100 to perform the OCT measurement with the scan pattern represented by the retrieved scan information.

In addition, the storage unit 212 may store scan information including information indicating the position of the subject's eye E to which the scan pattern is applied. In this case, the measurement controller 2111 retrieves the scan information associated with the newly input identification information from the storage unit 212, and controls the fundus camera unit 2 and the OCT unit 100 so as to apply the scan pattern represented by the retrieved scan information to the position of the subject's eye E represented by the scan information. The scan information may include a fixation position or a position in the observation image.

As a result, the scan pattern employed in the past OCT measurement can also be applied to subsequent measurements. With this, it becomes possible to accurately perform the follow-up observation of the site of interest or the like.

The LCD 39 is an example of the "fixation target projection unit" according to the present embodiment. The fundus camera unit 2 and the OCT unit 100 are examples of the "measurement unit" according to the present embodiment. The CCD image sensor 35 or the CCD image sensor 38 is an example of the "imaging unit" according to the present embodiment. The "imaging unit" according to the present embodiment may further include an optical system or the like for generating fundus reflection light detected by the CCD image sensor 35 or by the CCD image sensor 38. The display unit 241 is an example of "display device" according to the present embodiment. The operation unit 242 is an example of the "operation unit" according to the present embodiment.

OPERATION EXAMPLES

The operation of the ophthalmic imaging apparatus 1 will be described.

(Operation Examples Related to Scan Pattern in Live Scan)

In the live scan, the OCT scan with the same scan pattern is iteratively performed. During the live scan, the fixation target is presented to the subject's eye E. As a result, substantially the same cross section can be iteratively scanned with OCT, and a moving image of the cross section thus obtained can be displayed in real time. Incidentally, by performing tracking in parallel with the live scan, it is possible to suppress the occurrence of a situation in which the iterative OCT scan deviates from the target cross section due to the influence of eye movements or the like.

The following operation example describes a case in which a scan pattern called "five line cross scan" is employed. The "five line cross scan" is a kind of cross scan.

Figure 4:
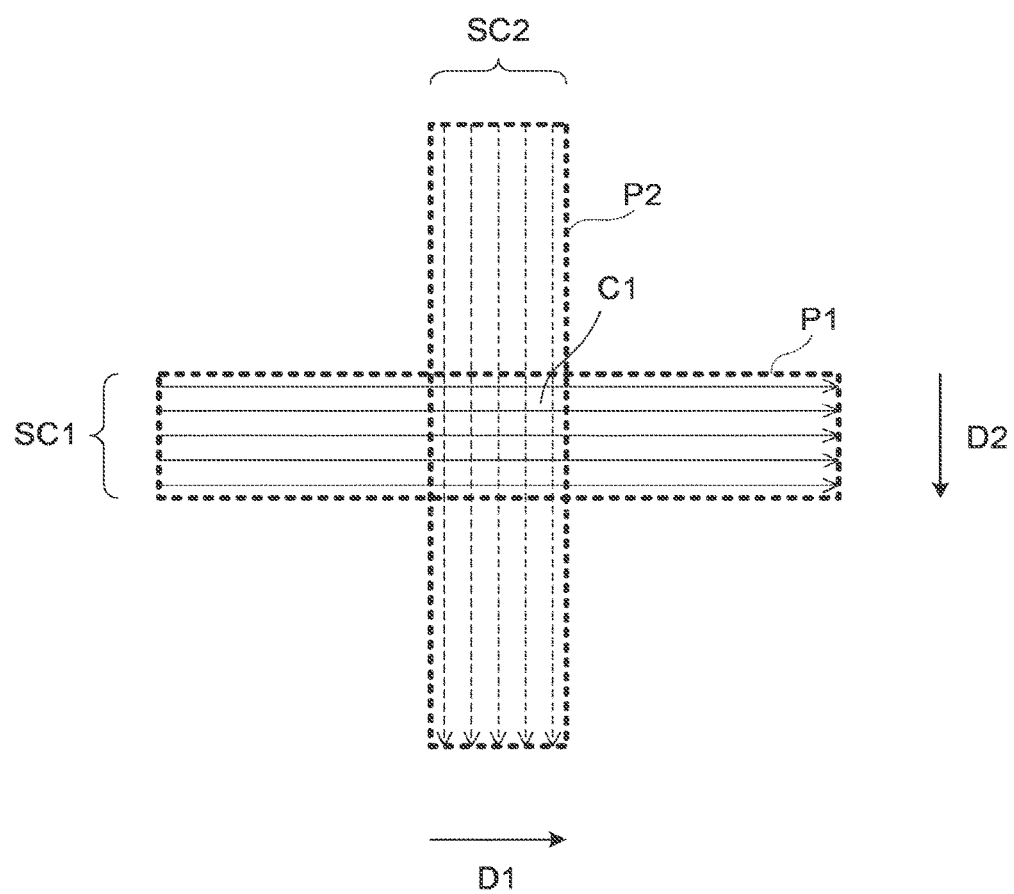
FIG. 4 is a schematic diagram for describing the operation of the ophthalmic imaging apparatus according to the embodiment.

FIG. 4 is an explanatory diagram of the "five line cross scan" according to the present embodiment. FIG. 4 schematically shows an example of the scan pattern of the "five line cross scan".

The "five line cross scan" is a scan pattern in which the first scan line group SC1 and the second scan line group SC2 are arranged in such a manner that they intersect one another. The first scan line group SC1 includes five scan lines parallel to each other and each extending in the first direction D1 (for example, in the x direction). The second scan line group SC2 includes five scan lines parallel to each other and each extending in the second direction D2 (for example, in the y direction) that is perpendicular to the first direction D1. The "five line cross scan" forms the first scan area P1 scanned by the first scan line group SC1 and the second scan area P2 scanned by the second scan line group SC2. The intersection area C1 between the first scan area P1 and the second scan area P2 is placed so as to overlap with, for example, the site of interest of the fundus Ef (e.g., the macula (fovea centralis), the optic nerve head, arbitrary position between the macula and the optic nerve head).

The arrows of the scan lines of the line segment shape constituting each scan line group indicate the scanning direction of the scan lines. The start points of and the end points of the scan lines represent the scanning start positions and the scanning end positions of the scan lines, respectively. The length of the scan lines indicates the length of the scanning along the scan lines. That is, the scan lines shown in FIG. 4 represent the scanning positions and the scanning directions of the scanning along the scan lines. For example, the boundary on the scanning start position side of the first scan area P1 is defined by the scanning start positions of the five scan lines. The boundary on the scanning end position side of the first scan area P1 is defined by the scanning end positions of the five scan lines. The boundary of the first scan area P1 parallel to the first direction D1 is defined by two scan lines arranged outermost among the five scan lines arranged in the second direction D2, or by the positions deviated from the two scan lines outward by a predetermined distance. The boundary of the second scan area P2 is also defined similarly to the first scan area P1.

FIG. 4 shows an example in which the first scan area P1 (i.e., the first scan line group SC1) is disposed in such a manner that the first scan area P1 is perpendicular to the second scan area P2 (i.e., the second scan line group SC2). In another example, the first scan area P1 may be disposed in such a manner that the first scan area P1 intersects the second scan area P2 (at an arbitrary angle) rather than being perpendicular to the second scan area P2.

In addition, FIG. 4 shows an example in which each of the first scan area P1 and the second scan area P2 is scanned along five scan lines, but the number of scan lines is not limited to this. For example, at least one of the first scan area P1 and the second scan area P2 may be an area(s) scanned along one scan line or three scan lines.

In addition, the "five line cross scan" is an example of a scan pattern corresponding to two or more scan lines representing scan positions and scan directions and having two scan areas arranged such that at least two of the two or more scan lines intersect one another. It is also possible to apply a scan pattern in which three or more scan areas intersect one another, like the radial scan, to the embodiment During the scan, the first scan and the second scan are performed alternately. The first scan is along at least one scan line constituting the first scan line group SC1. The second scan is along at least one scan line constituting the second scan line group SC2. The phrase "to perform the first scan and the second scan alternately" includes not only the case of alternately performing the first scan once and the second scan once but also the case of alternatively performing the first scan one or more times and the second scan one or more times. Further, the group of scan lines in each scan area are cyclically scanned in a predetermined order.

In addition, when the wavelength of the measurement light for scanning in the first direction D1 and the wavelength of the measurement light for scanning in the second direction D2 are different from one another, the first scan and the second scan may be performed simultaneously.

In the present embodiment, the relative position between the first scan area P1 and the second scan area P2 can be changed automatically or manually.

In the case of automatically changing the relative position, the data processor 230 analyzes the observation image of the subject's eye E to specify the position of a specific site (e.g., the macula, the fovea centralis, the optic nerve head, a blood vessel, a lesion site, etc.). Further, the data processor 230 changes the relative position between the first scan area P1 and the second scan area P2 such that they pass through a site determined by the specific site or by a site determined by the specific site, thereby setting a scan position. Here, for example, the scan position is set such that the intersection area C1 between the first scan area P1 and the second scan area P2 is made to coincide with the specific site through the analysis described above. The relative position is changed by moving each scan area in a predetermined direction. For example, the moving direction of the first scan area P1 is the first direction D1 or the opposite direction thereto. Also, for example, the moving direction of the second scan area P2 is the second direction D2 or the opposite direction thereto. The movement of the scan area includes at least one of parallel movement (i.e., translation) and rotation movement. The movement control of the scan position through such movements of the scan area is performed by changing the setting for controlling the optical scanner so that the measurement controller 2111 moves scan lines in each scan area in the same direction by the same amount (i.e., the same distance) according to the content of the change of the scan position (i.e., movement direction and movement amount).

On the other hand, in the case of manually changing the relative position, the user designates a scan area to be moved using the user interface 240 and moves the designated scan area. Hereinafter, referring to FIG. 5 to FIG. 9B, an operation example in the case where the relative position is manually changed will be described.

Figure 5:
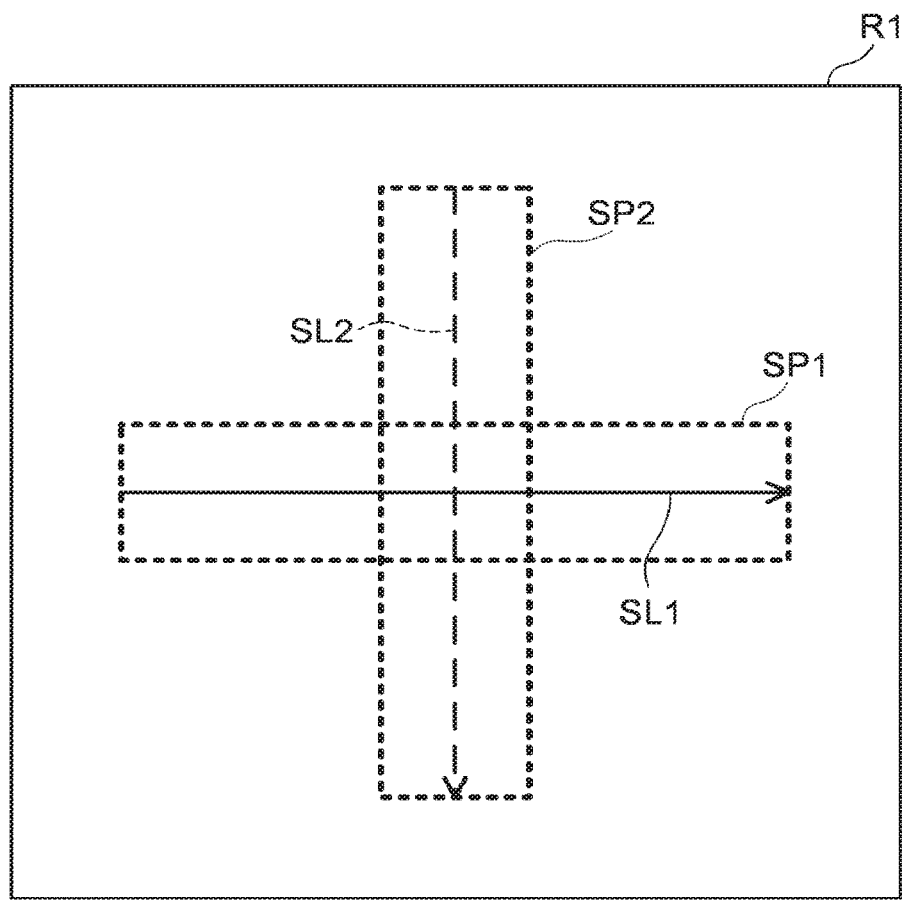
FIG. 5 is a schematic diagram for describing the operation of the ophthalmic imaging apparatus according to the embodiment.

FIG. 5 schematically shows an example of the screen of the display unit 241 for changing the relative positions between the first scan area P1 and the second scan area P2.

The user selects a scan pattern using the user interface 240 with a known method. When the selected scan pattern is the "five line cross scan", the display controller 2112 superimposes the scan pattern images SP1 and SP2 corresponding to the scan pattern of the "five line cross scan" on the moving image of the subject's eye E generated based on the fundus reflection light detected by the CCD image sensor 35 according to the initial position and the initial direction within the display area of the display unit 241, and displays the scan pattern images SP1 and SP2 and the moving image. In another example, the display controller 2112 superimposes the scan pattern images SP1 and SP2 on the moving image of the subject's eye E based on the fundus reflection light detected by the CCD image sensor 35 according to the scan position and the scan direction in the last examination within the display area of the display unit 241, and displays the scan pattern images SP1 and SP2 and the moving image. The scan pattern images SP1 and SP2 are images displayed on the display unit 241 corresponding to two or more scan lines (e.g., five scan lines in each of the two directions in the present embodiment) representing the scan position and the scan direction. In addition, the scan pattern images SP1 and SP2 are images arranged such that at least two of the two or more scan lines intersect one another. In the following description, the first scan area P1 and the corresponding scan pattern image SP1 displayed on the display unit 241 may be treated in the same way. Similarly, the second scan area P2 and the corresponding scan pattern image SP2 displayed on the display unit 241 may be treated in the same way.

For example, as shown in FIG. 5, the scan pattern image may be an image SP1 representing the boundary (i.e., the contour) of the first scan area P1 constituting the concerned scan pattern and an image SP2 representing the boundary (i.e., the contour) of the second scan area P2 constituting the concerned scan pattern. The scan pattern image may also be, for example, a scan line image SL1 corresponding to the first scan line group SC1 within the first scan area P1 and a scan line image SL2 corresponding to the second scan line group SC2 within the second scan area P2 as shown in FIG. 5. Alternatively, the scan pattern image may be an image of the vicinity of the scan start positions of and an image of the vicinity of the scan end positions of the scan lines within each scan area. With such a scan pattern image, the observation of the site of interest is not disturbed. This scan pattern image may further include an image representing the intersection area C1. For example, in FIG. 5, both set of the images SP1 and SP2, and the images SL1 and SL2 are shown as the scan pattern image; however, displaying any one of them on the display unit 241 serves the purpose.

Further, as shown in FIG. 5, the display controller 2112 can also display the display area R1 corresponding to the scannable area of the ophthalmic imaging apparatus 1 within the display area of the display unit 241 on which the scan pattern images SP1 and SP2 are displayed. This makes it easy to grasp the movable areas of the scan pattern image SP1 (i.e., the first scan area P1) and the scan pattern image SP2 (i.e., the second scan area P2). Therefore, the user can change the relative position between the scan pattern images SP1 and SP2 while confirming the movable areas. In the following description, the scannable area and the corresponding display area R1 displayed on the display unit 241 may be treated in the same way.

The operation unit 242 receives various kinds of operations from the user. For example, the operation unit 242 receives an operation for designating any of the scan pattern images SP1 and SP2 (referred to as a first designation operation), and an operation for performing the parallel movement or the rotation movement of the scan pattern image designated by the designation operation (referred to as a first movement operation). The designation operation is performed, for example, by selecting a scan pattern from a group of scan pattern images corresponding to a group of scan areas that can be moved. The movement operation is performed by designating, for example, a movement direction and a movement amount of the scan pattern image designated by the designation operation. Further, when the touch panel functions as the display unit 241 and the operation unit 242, the screen of the display unit 241 functions as an operation screen. In this case, the designation operation is performed, for example, by an operation of touching a position in the operation screen associated with a desired scan pattern image from the group of movable scan pattern images. The movement operation is performed by, for example, a drag operation on the operation screen according to a movement direction and a movement amount of the scan pattern image designated by the designation operation.

Figure 6A:
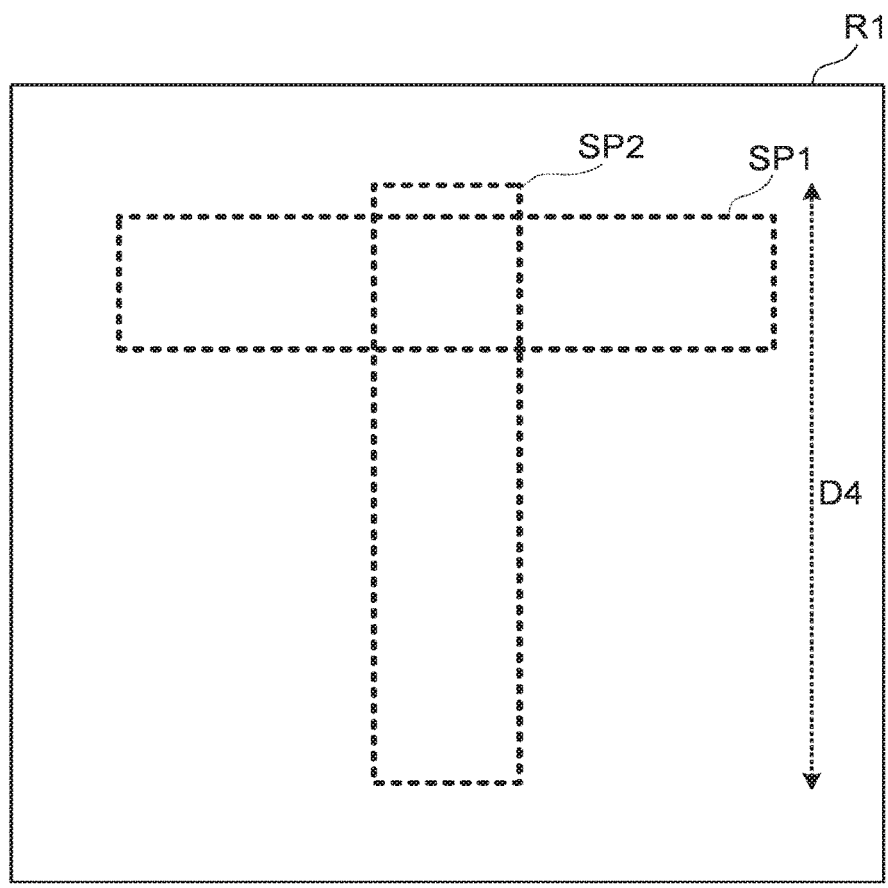
FIG. 6A is a schematic diagram for describing the operation of the ophthalmic imaging apparatus according to the embodiment.

A case where the first scan area P1 is translated will be described with referring to FIG. 6A. In FIG. 6A, parts similarly configured to those in FIG. 5 are denoted by the same reference numerals, and the description thereof is omitted unless it is necessary.

In the state shown in FIG. 5, when the user performs the designation operation of the scan pattern image SP1 using the operation unit 242, the measurement controller 2111 (the main controller 211) specifies a first scan area P1 based on the contents of the operation performed using the operation unit 242. Subsequently, when the user performs, using the operation unit 242, the movement operation of the scan pattern image SP1 for moving it by a predetermined movement amount in the movement direction D4, the measurement controller 2111 determines the position of the first scan area P1 moved by the predetermined movement amount in the movement direction D4 based on the contents of the operation performed using the operation unit 242. The display controller 2112 displays the scan pattern image SP1 at the display position corresponding to the position of the first scan area P1 determined by the measurement controller 2111 (i.e., the state shown in FIG. 6A). As a result, the display controller 2112 can change the display position of the scan pattern image corresponding to the scan area according to the movement operation. Note that although the movement direction D4 is shown as a direction parallel to the second direction D2, it may be an arbitrary direction along the surface of the fundus Ef. When the position of the scan pattern image SP1 after movement is determined, the measurement controller 2111 controls the fundus camera unit 2 and the OCT unit 100 to perform OCT measurement while controlling the scan position by the optical scanner 42 based on the scan lines in the scan areas P1 and P2 corresponding to the scan pattern images SP1 and SP2 after the relative position is changed.

Figure 6B:
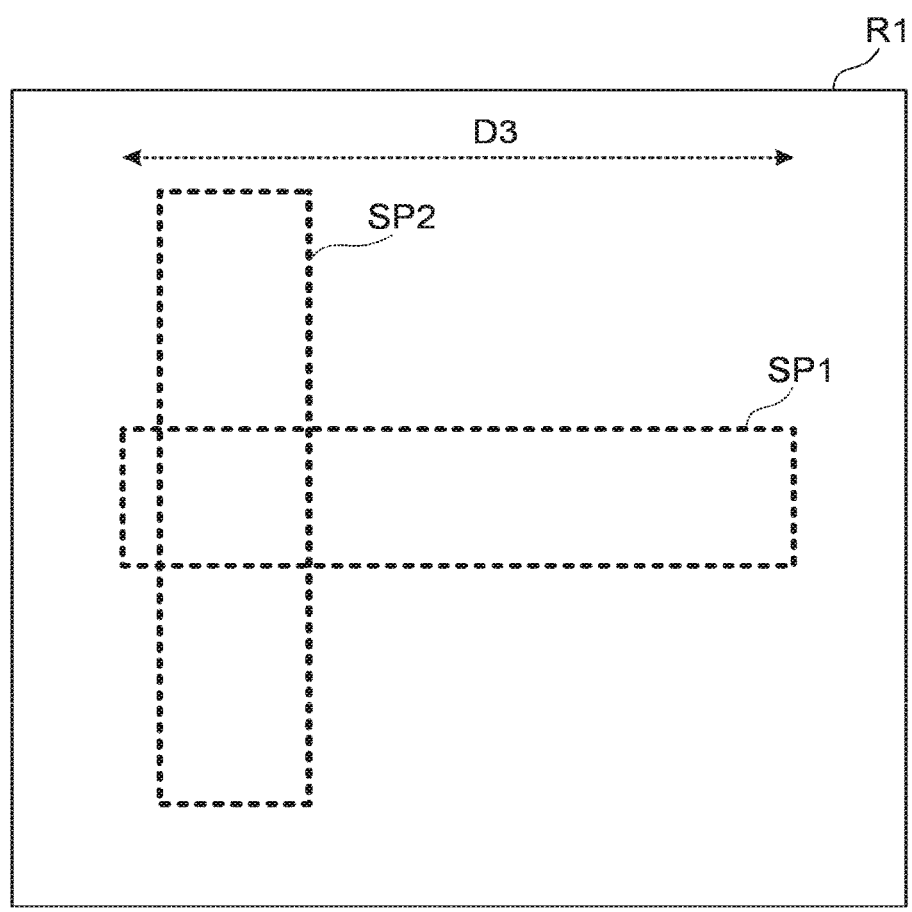
FIG. 6B is a schematic diagram for describing the operation of the ophthalmic imaging apparatus according to the embodiment.

A case where the second scan area P2 is translated will be described with referring to FIG. 6B. In FIG. 6B, parts similarly configured to those in FIG. 5 are denoted by the same reference numerals, and the description thereof is omitted unless it is necessary.

As in FIG. 6A, in the state shown in FIG. 5, when the user designates the scan pattern image SP2 using the operation unit 242, the measurement controller 2111 (the main controller 211) specifies a second scan area P2 based on the contents of the operation performed using the operation unit 242. Subsequently, when the user performs the movement operation of the scan pattern image SP2 for moving it by a predetermined movement amount in the movement direction D3 using the operation unit 242, the measurement controller 2111 determines the position of the second scan area P2 moved by the predetermined movement amount in the movement direction D3 based on the contents of the operation performed using the operation unit 242. The display controller 2112 displays the scan pattern image SP2 at the display position corresponding to the position of the second scan area P2 determined by the measurement controller 2111 (i.e., the state shown in FIG. 6B). Note that although the movement direction D3 is shown as a direction parallel to the first direction D1, it may be an arbitrary direction along the surface of the fundus Ef. When the position of the scan pattern image SP2 after movement is determined, the measurement controller 2111 controls the fundus camera unit 2 and the OCT unit 100 to perform OCT measurement while controlling the scan position by the optical scanner 42 based on the scan lines in the scan areas P1 and P2 corresponding to the scan pattern images SP1 and SP2 after the relative position is changed.

Like the case of the parallel movement described above, the scan pattern images SP1 and SP2 (i.e., the first scan area P1 and the second scan area P2) can also be rotated with respect to an arbitrary reference position within the display area R1 corresponding to the scannable area. In the case of performing the rotation movement, for example, the user performs the following operations: an operation of designating a rotation center position; an operation of designating a scan pattern image to be rotated; and an operation of rotating the designated scan pattern image by a desired angle. It should be noted that it is also possible to adopt a configuration in which rotation movement is performed around a predetermined position. For example, any of the following configurations can be adopted: a configuration for setting the center position of the designated scan pattern image to be the center of rotation; a configuration for setting the center position of the intersection area of the scan pattern images to be the center of rotation; and a configuration for setting a predetermined site of interest (e.g., the fovea centralis) to be the center of rotation.

In addition, the user can integrally move the scan pattern images SP1 and SP2 (i.e., the first scan area P1 and the second scan area P2) by the use of the user interface 240. The processing in this case is performed in the following manner, for example.

The operation unit 242 receives an operation for designating the scan pattern images SP1 and SP2 (referred to as a second designation operation), and operation movement for performing parallel movement of or for performing rotation movement of the scan pattern image designated by the designation operation (referred to as a second designation operation). The designation operation is performed, for example, by designating an intersection area where at least two of the two or more scan pattern images intersect on another. The movement operation is performed by designating, for example, a movement direction and a movement amount of the scan pattern image designated by the designation operation. Further, when the touch panel functions as the display unit 241 and the operation unit 242, the designation operation is performed, for example, by the touch panel operation with respect to the position within a screen (in the moving image) different from the positions of the scan pattern images SP1 and SP2 displayed in the display area of the display unit 241. Further, the designation operation may be performed, for example, by a touch operation with respect to the intersection area where at least two of the two or more scan pattern images intersect one another. The movement operation is performed, for example, by a drag operation with respect to the position designated by the touch operation described above.

Figure 6C:
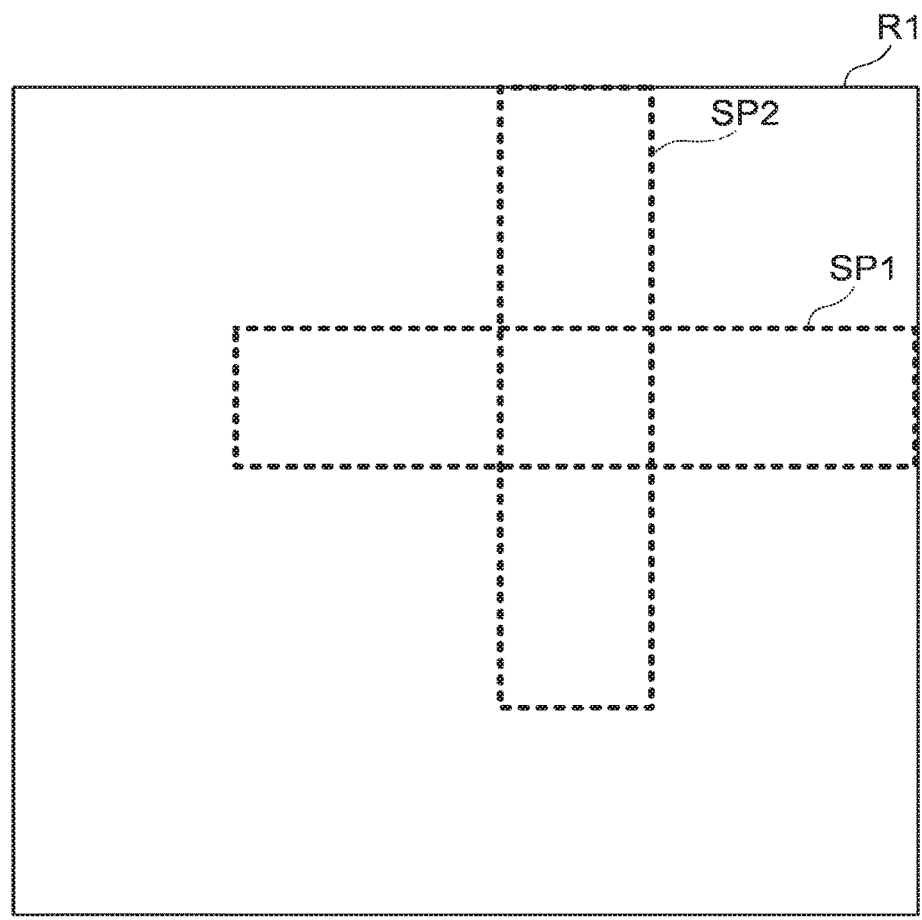
FIG. 6C is a schematic diagram for describing the operation of the ophthalmic imaging apparatus according to the embodiment.

A case where the first scan area P1 and the second scan area P2 are integrally moved will be described with further referring to FIG. 6C. In FIG. 6C, parts similarly configured to those in FIG. 5 are denoted by the same reference numerals, and the description thereof is omitted unless it is necessary.

In the state shown in FIG. 5, when the user designates the scan pattern images SP1 and SP2 integrally using the operation unit 242, the measurement controller 2111 (main controller 211) specifies the first scan area P1 and the second scan area P2 based on the contents of the operation performed using the operation unit 242. Subsequently, when the user performs the movement operation of the scan pattern images SP1 and SP2 for moving them by a predetermined movement amount in an arbitrary direction within the display area of the display unit 241 using the operation unit 242, the measurement controller 2111 determines the positions of the first scan area P1 and the second scan area P2 moved by the predetermined movement amount in the designated movement direction based on the contents of the operation performed using the operation unit 242. The display controller 2112 displays the scan pattern image SP1 at the display position corresponding to the position of the first scan area P1 determined by the measurement controller 2111, and displays the scan pattern image SP2 at the display position corresponding to the position of the second scan area P2 determined by the measurement controller 2111 (i.e., the state shown in FIG. 6C). When the positions of the scan pattern images SP1 and SP2 after the movement are determined, the measurement controller 2111 controls the scan position by the optical scanner 42 based on the scan lines in the scan areas P1 and P2 corresponding to the scan pattern images SP1 and SP2 after they have been integrally moved. In this manner, the measurement controller 2111 controls the fundus camera unit 2 and the OCT unit 100 to perform OCT measurement.

In FIG. 6C, in the case where the scan pattern is constituted by two or more scan areas, the user can integrally move at least part of two or more scan pattern images corresponding to two or more scan areas.

The movement of the scan pattern images (i.e., the scan areas) described above may be limited within the scannable area of the ophthalmic imaging apparatus 1. More specifically, the measurement controller 2111 obtains the positions of the scan pattern images moved as described above, and determines whether or not the entire scan pattern images after the movement to the obtained positions are included within the display area corresponding to the scannable area. When it is determined that the entire scan pattern images after the movement are not included in the display area, the measurement controller 2111 obtains the positions of the scan pattern images that have undergone the movement operation so that the entire scan pattern images after the movement fall within the display area. As a result, the display controller 2112 can change the display positions of the scan pattern images SP1 and SP2 within the display area R1 of the display unit 241 corresponding to the scannable area.

Further, when a request to move a scan pattern image, beyond a scannable area, of a predetermined movement amount in a predetermined movement direction has been performed using the operation unit 242, the ophthalmic imaging apparatus 1 can move the scan pattern image as follows.

Figure 7:
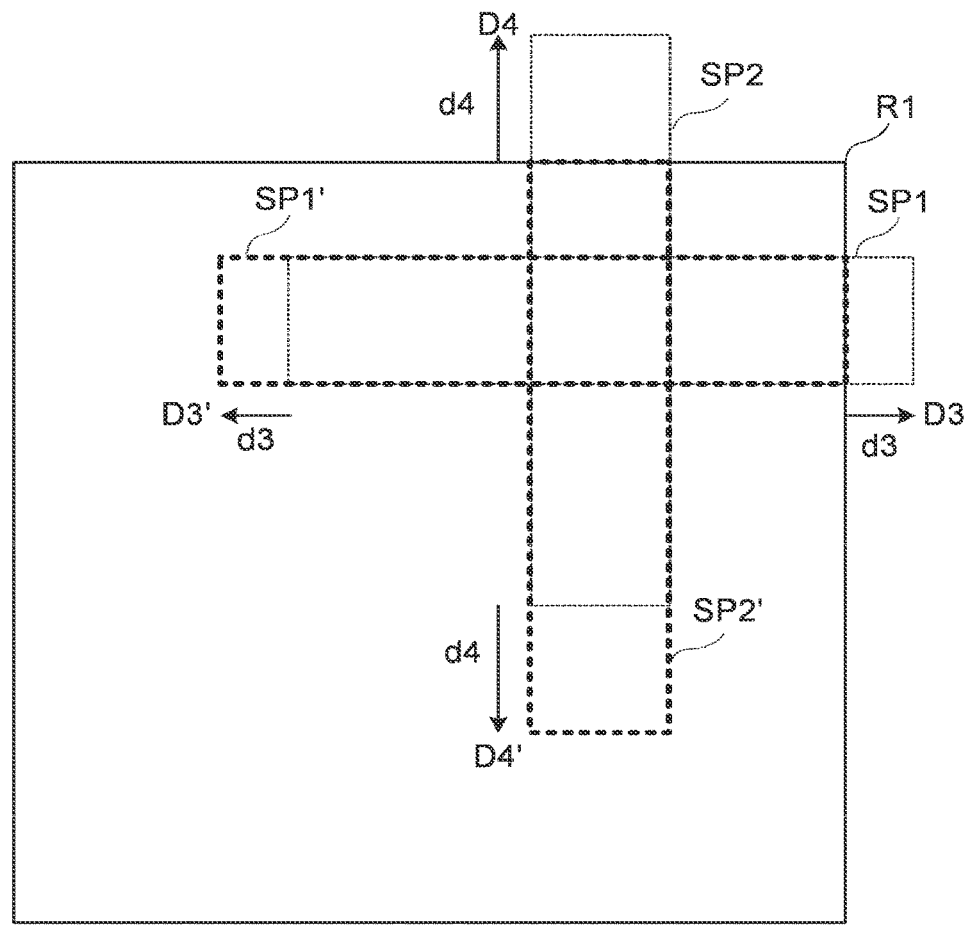
FIG. 7 is a schematic diagram for describing the operation of the ophthalmic imaging apparatus according to the embodiment.

A first operation example in the case where a request to move the scan pattern image is made will be described with further referring to FIG. 7. In FIG. 7, parts similarly configured to those in FIG. 5 are denoted by the same reference numerals, and the description thereof is omitted unless it is necessary.

In the state shown in FIG. 5, when a movement request of the scan pattern image SP1 beyond the scannable area (i.e., the display area R1) of the movement amount d3 (first movement amount) in the movement direction D3 (first movement direction) is performed by using the operation unit 242, the measurement controller 2111 obtains the position at which the scan pattern image SP1 makes contact with the edge of the scannable area, and then obtains the movement position that is displaced from the obtained contact position by the movement amount d3 in the direction D3' (second movement direction) opposite to the movement direction D3. The display controller 2112 controls the display unit 241 to display the moved scan pattern image SP1' at the display position on the display unit 241 corresponding to the movement position obtained by the measurement controller 2111 (i.e., the state shown in FIG. 7). Similarly, when a movement request of the scan pattern image SP2 beyond the scannable area (i.e., the display area R1) of the movement amount d4 in the movement direction D4 is performed by using the operation unit 242, the measurement controller 2111 obtains the position at which the scan pattern image SP2 makes contact with the edge of the scannable area in the movement path, and obtains the movement position that is displaced from the obtained contact position by the movement amount d4 in the direction D4' opposite to the movement direction D3. The display controller 2112 controls the display unit 241 to display the moved scan pattern image SP2' at the display position on the display unit 241 corresponding to the movement position obtained by the measurement controller 2111 (i.e., the state shown in FIG. 7).

As described above, when the requested movement destination is located outside the scannable area by the first movement amount in the first movement direction, the display controller 2112 can change the display position of the scan pattern image in contact with the edge of the scannable area in the second movement direction which is opposite to the first movement direction by the first movement amount. With such control, even when a movement request of a scan pattern beyond the scannable area is made, the ophthalmic imaging apparatus 1 can place the intersection area at an arbitrary position within the scannable area and can perform scanning of the site of interest without reducing the dimension of the scan area.

Figure 8A:
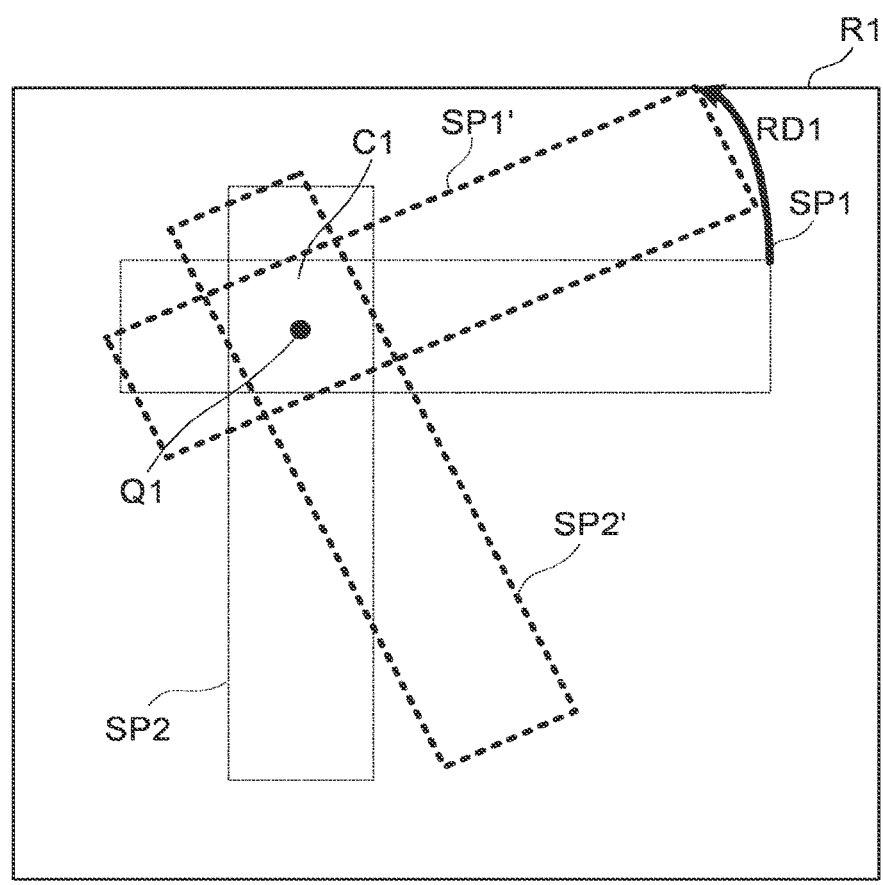
FIG. 8A is a schematic diagram for describing the operation of the ophthalmic imaging apparatus according to the embodiment.
Figure 8B:
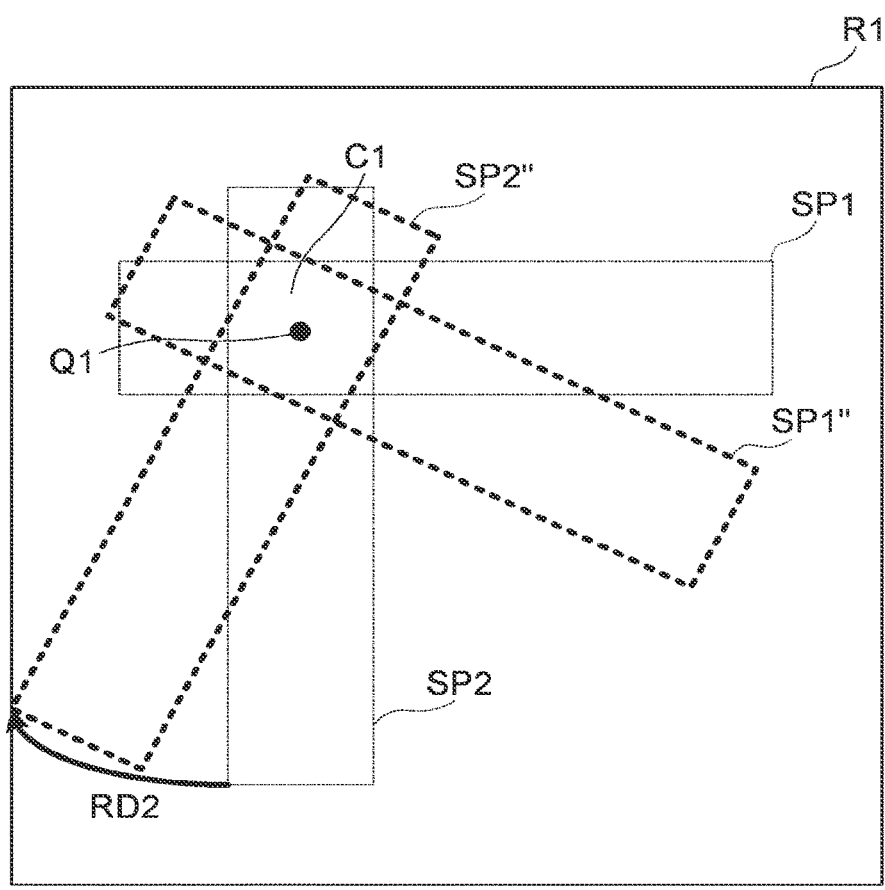
FIG. 8B is a schematic diagram for describing the operation of the ophthalmic imaging apparatus according to the embodiment.

A second operation example in the case where a movement request of the scan pattern image is made will be described with further referring to FIG. 8A and FIG. 8B. FIG. 8A and FIG. 8B show an operation example in the case where a request for the rotation movement with the position Q1 in the intersection area C1 as a reference is made. In FIG. 8A and FIG. 8B, parts similarly configured to those in FIG. 5 are denoted by the same reference numerals, and the description thereof is omitted unless it is necessary.

In the state shown in FIG. 5, when a movement request of the scan pattern image SP1 beyond the scannable area (i.e., the display area R1) in the predetermined rotation direction RD1 is performed by using the operation unit 242, the measurement controller 2111 obtains, as shown in FIG. 8A, the position at which the scan pattern image SP1 makes contact with the edge of the scannable area (referred to as a contact position). The display controller 2112 controls the display unit 241 to display the scan pattern image SP1' after rotation at the display position on the display unit 241 corresponding to the contact position obtained by the measurement controller 2111. Similarly, the display controller 2112 controls the display unit 241 to display the scan pattern image SP2' after rotation at the display position on the display unit 241 corresponding to the contact position obtained by the measurement controller 2111 (i.e., the state shown in FIG. 8A).

Further, in the state shown in FIG. 5, when a movement request of the scan pattern image SP2 beyond the scannable area (i.e., the display area R1) in the predetermined rotation direction RD2 is performed by using the operation unit 242, the measurement controller 2111 obtains, as shown in FIG. 8B, the position at which the scan pattern image SP2 makes contact with the edge of the scannable area (referred to as a contact position). The display controller 2112 controls the display unit 241 to display the scan pattern image SP2" after rotation at the display position on the display unit 241 corresponding to the contact position obtained by the measurement controller 2111. Similarly, the display controller 2112 controls the display unit 241 to display the scan pattern image SP1" after rotation at the display position on the display unit 241 corresponding to the contact position obtained by the measurement controller 2111 (i.e., the state shown in FIG. 8B).

As described above, when a request to move the scan pattern image beyond the scannable area is made by using the operation unit, the display controller can stop the movement of the display position of at least the scan pattern image that has touched the edge of the scannable area at the contact position. With such control, even when a movement request of a scan pattern beyond the scannable area is made, the ophthalmic imaging apparatus 1 can place the intersection area at an arbitrary position within the scannable area, and can perform scanning of the site of interest without reducing the dimension of the scan area.

FIG. 8A and FIG. 8B shows the case in which the scan pattern images SP1 and SP2 (i.e., the first scan area P1 and the second scan area P2) are integrally rotated, but the present embodiment is not limited thereto. For example, in FIG. 8A, only the scan pattern image SP1 (i.e., the first scan area P1) may be rotated while fixing the scan pattern image SP2 (i.e., the second scan area P2). In contrast, in FIG. 8B, only the scan pattern image SP1 may be rotated while fixing the scan pattern image SP1. Further, in case of translating the scan pattern images SP1 and SP2, as shown in FIG. 8A and FIG. 8B, the ophthalmic imaging apparatus 1 may stop the movement of the display position of the scan pattern image in contact with the edge of the scannable area at the contact position.

In addition, it is also possible to perform the parallel movement of the scan pattern after the rotation movement described above.

A third operation example in the case where a request to move the scan pattern image is made will be described with further referring to FIG. 9A and FIG. 9B.

Figure 9A:
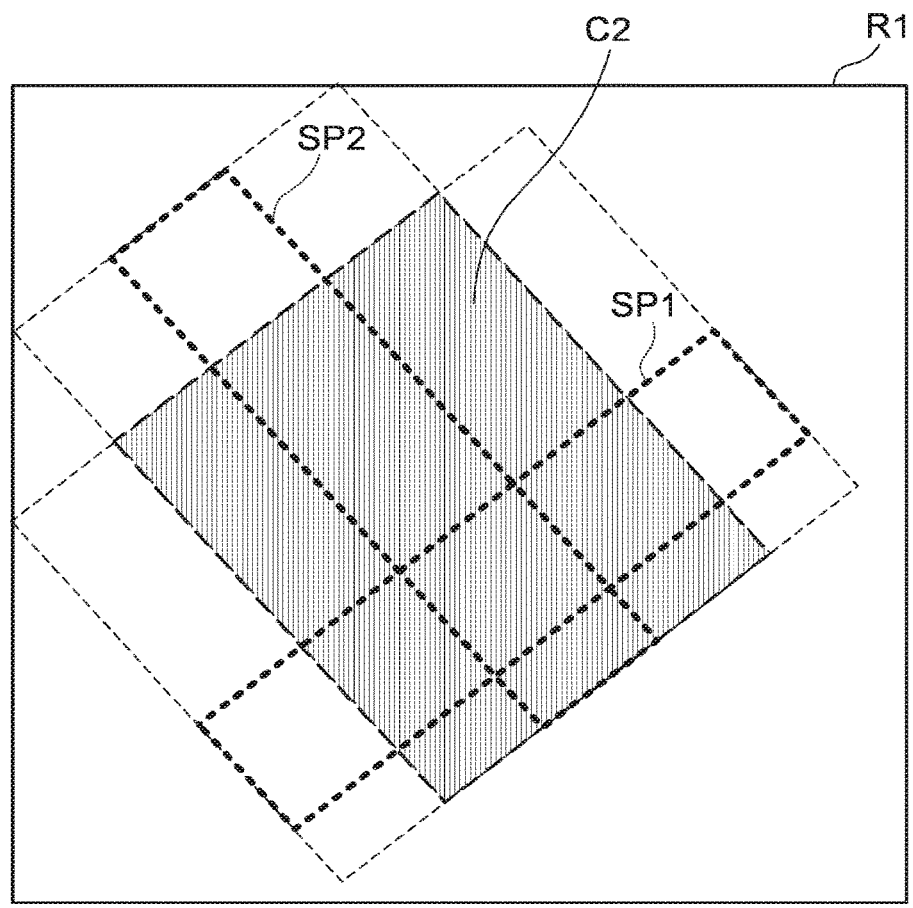
FIG. 9A is a schematic diagram for describing the operation of the ophthalmic imaging apparatus according to the embodiment.

In the state shown in FIG. 5, when a rotation movement request for the scan pattern images SP1 and SP2 is made in the manner shown in FIG. 9A, even in a state in which the scan pattern images SP1 and SP2 after rotation are not parallel to the boundary of the display area R1 corresponding to the scannable area, at least one of the scan pattern images SP1 and SP2 can be translated. Here, rotation movement may also be performed. For example, in the case shown in FIG. 9A, the intersection area C1 of the scan pattern images SP1 and SP2 can be located at an arbitrary position within the locatable area C2.

Figure 9B:
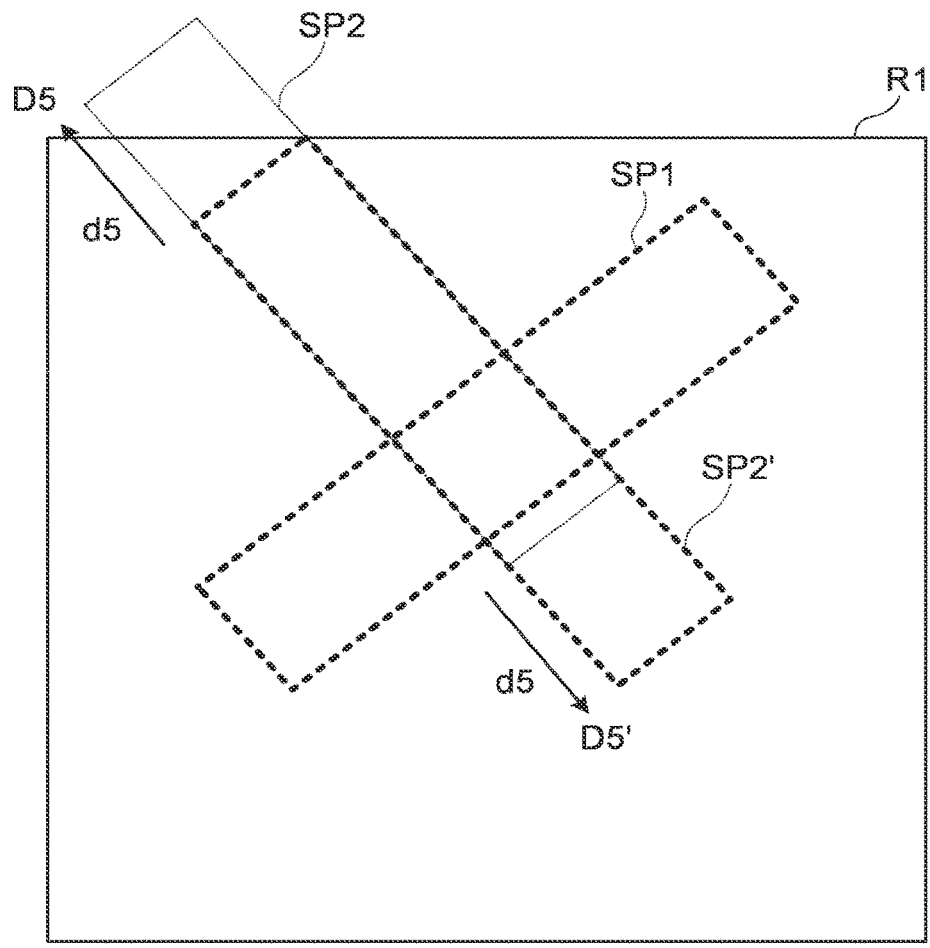
FIG. 9B is a schematic diagram for describing the operation of the ophthalmic imaging apparatus according to the embodiment.

Further, as shown in FIG. 9B, when a request to move the scan pattern image SP2 beyond the scannable area (i.e., the display area R1) is made by using the operation unit 242, it is possible to move the scan pattern as in FIG. 8A or 8 B. More specifically, when a movement request of the scan pattern image SP2 beyond the scannable area (i.e., display area R1) of the movement amount d5 in the movement direction D5 is made by using the operation unit 242, the measurement controller 2111 obtains the position where the scan pattern image SP2 makes contact with the edge of the scannable area, and determines the movement position that is displaced from the contact position by the movement amount d5 in the direction D5' opposite to the movement direction D5. The display controller 2112 controls the display unit 241 to display the scan pattern image SP2' after the movement at the display position on the display unit 241 corresponding to the movement position determined by the measurement controller 2111.

As described above, the ophthalmic imaging apparatus 1 can perform movement in an arbitrary direction with respect to a scan pattern of an arbitrary orientation. Therefore, for example, it is possible to easily observe a cross sectional image along a desired site such as a straight line connecting the macular portion and the optic nerve head, a cross sectional image traversing a desired path, and the like.

(Other Operation Examples Related to Scan Patterns)

The user can change the size of the scan pattern used for the live scan and the locations of the scan lines within the scan area by using the user interface 240.

The operation unit 242 receives a size changing operation from the user for changing the size of at least part of two or more scan pattern images. Examples of the size of the scan pattern image include the length in a predetermined direction, the width, the area, and the like of the scan pattern image. The size changing operation is performed, for example, by inputting a new size value for a size that has been selected from among options of the size, or by changing the boundary portion of the scan pattern image. Further, when the touch panel functions as the display unit 241 and as the operation unit 242, for example, the size changing operation is performed by designating the boundary of the scan pattern image displayed within the display area of the display unit 241 by a touch operation, and by moving the designated boundary by a drag operation. Subsequently, the measurement controller 2111 obtains new display positions of the first scan area P1 and of the second scan area P2 designated to be resized on the basis of the contents of the operation on the operation unit 242. Note that the measurement controller 2111 may arrange scan lines at regular intervals within the scan area in accordance with the size of the scan area after the size change, for example. The display controller 2112 displays the scan pattern image SP1 in the display position corresponding to the position of the first scan area P1 determined by the measurement controller 2111, and displays the scan pattern image SP2 in the display position corresponding to the position of the second scan area P2 determined by the measurement controller 2111. When the position after the size change is determined, the measurement controller 2111 controls the fundus camera unit 2 and the OCT unit 100 to perform OCT measurement while controlling the scan position by the optical scanner 42 based on the scan lines in the scan areas P1 and P2 corresponding to the scan pattern images SP1 and SP2 after the size change.

As described above, the display controller 2112 can change the display size of at least part of two or more scan pattern images whose sizes have been changed by using the operation unit 242 according to the size change operation. Thus, it is possible to change the size of the scan pattern in accordance with the site of interest, and the user can easily observe the desired site of interest based on the scan pattern of a suitable size within the scannable area. When a size change request is made so that the scan area after the size change protrudes from the scannable area, any of the processes described above may be performed. More specifically, it is possible to accept only the size change request within the scannable area, or to add the protruding portion to the opposite side.

In addition, the user can change the arrangement intervals of the scan lines in the scan area or the like by using the user interface 240.

The operation unit 242 receives an operation performed by the user for changing relative positions between two or more scan lines. Changing the relative position between the two or more scan lines includes changing the intervals between adjacent scan lines, changing the scan positions (e.g., the scan start position or the scan end position) of adjacent scan lines, and the like. The change of the relative position between the two or more scan lines may be a concept including the change of the scan directions. The operation for changing the relative position between the two or more scan lines is carried out, for example, by designating a desired scan line, and moving the designated scan line in a state where the scan line adjacent to the designated scan line is fixed. When the touch panel functions as the display unit 241 and the operation unit 242, the operation for changing the relative positions between the two or more scan lines includes a touch operation for designating a desired scan line, and a drag operation for moving the designated scan line in a state where the scan line adjacent to the designated scan line is fixed.

The measurement controller 2111 controls the scan position by the optical scanner 42 based on the two or more scan lines whose relative positions have been changed so that the fundus camera unit 2 and the OCT unit 100 perform the OCT measurement. As a result, it is possible to freely change the density of the scan lines, and the user can perform detailed observation according to a desired site of interest.

(Operation Examples Related to Display)

Figure 10:
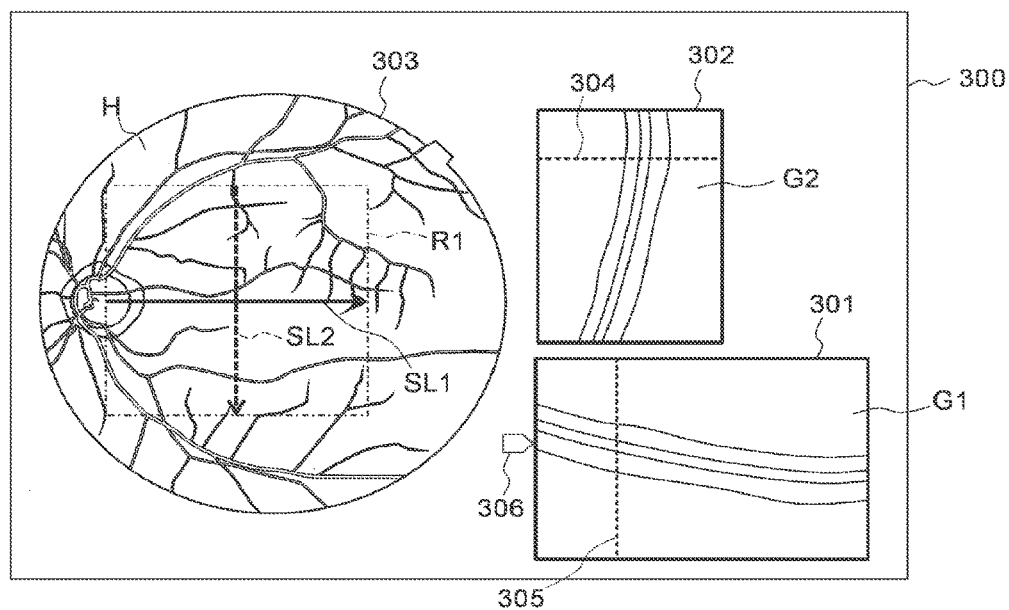
FIG. 10 is a schematic diagram for describing the operation of the ophthalmic imaging apparatus according to the embodiment.

An example of information display is shown in FIG. 10. In the present example, the case where the scan pattern of the "five line cross scan" is applied will be described. However, a similar display process can be performed when another scan pattern is applied.

A display screen 300 shown in FIG. 10 is displayed on the display unit 241 by the display controller 2112. The display screen 300 includes a first moving image display area 301, a second moving image display area 302, and a front image display area 303.

In the front image display area 303, the observation image H of the fundus Ef is displayed. The observation image H is an infrared moving image. In the front image display area 303, a scan line image SL1 and a scan line image SL2 are further displayed. The scan line image SL1 corresponds to the first scan line group SC1 in the first scan area P1, and the scan line image SL2 corresponds to the second scan line group SC2 in the second scan area P2. In the present example, the scan line images SL1 and SL2 are displayed over the observation image H. In addition, the display area R1 corresponding to the scannable area is displayed over the observation image H. The display area R1 may be displayed or may not be displayed.

In the first moving image display area 301, a moving image (first moving image) G1 is displayed. The first moving image G1 is obtained through iterative scanning along the first scan line group SC1 in the first scan area P1 corresponding to the scan line image SL1. In the second moving image display area 302, a moving image (second moving image) G2 is displayed. The second moving image G2 is obtained through iterative scanning along the second scan line group SC2 in the second scan area P2 corresponding to the scan line image SL2. As described above, in the present example, the first scan along at least one scan line constituting the first scan line group SC1 and the second scan along at least one scan line constituting the second scan line group SC2 are performed.

In order to display the first moving image G1, the display controller 2112 displays the cross sectional image sequentially formed by the image forming unit 220 from the data obtained by the first scan at a predetermined frame rate (for example, at a frame rate equal to or a multiple of the repetition rate of the first scan) in the moving image display area 301. Similarly, in order to display the second moving image G2, the display controller 2112 displays the cross sectional image sequentially formed by the image forming unit 220 from the data obtained by the second scan at a predetermined frame rate (for example, at a frame rate equal to or a multiple of the repetition rate of the second scan) in the moving image display area 302.

The first moving image display area 301 is arranged in an orientation corresponding to the scan line image SL1. In the present example, the first moving image display area 301 is of a rectangular shape, and the orientations of the upper side and the lower side of the first moving image display area 301 coincide with the orientation of the scan line image SL1. That is, in FIG. 10, the scan line image SL1 is a line segment (or an arrow) extending in the left-right direction, and the upper side and the lower side of the first moving image display area 301 also extend in the left-right direction. In the observation image H, the horizontal direction corresponds to the x direction and the vertical direction corresponds to the y direction. In addition, in the first moving image display area 301, the directions (i.e., the left and right directions) along the upper side and the lower side correspond to the x direction, and the left side and the right side (i.e., the up and down direction) correspond to the y direction. Therefore, the orientation of the scan line image SL1 displayed on the observation image H (i.e., the x direction) and the orientation of the cross section of the first moving image G1 displayed in the first moving image display area 301 (i.e., the x direction) coincide with one another.

Likewise, the second moving image display area 302 is arranged in an orientation corresponding to the scan line image SL2. In the present example, the second moving image display area 302 is of a rectangular shape, and the orientations of the left side and the right side of the second moving image display area 302 coincide with the orientation of the scan line image SL2. That is, in FIG. 10, the scan line image SL2 is a line segment (or an arrow) extending in the vertical direction, and the left side and the right side of the second moving image display area 302 extend in the vertical direction. As described above, in the observation image H, the horizontal direction corresponds to the x direction and the vertical direction corresponds to the y direction. In addition, in the second moving image display area 302, the directions of the left side and the right side (i.e., the vertical direction) correspond to the y direction, and the upper side and the lower side (i.e., the left and right directions) correspond to the y direction. Therefore, the direction of the scan line image SL2 displayed on the observation image H (i.e., the y direction) and the direction of the cross section of the second moving image G2 displayed in the second moving image display area 302 (i.e., the y direction) coincide with one another.

Further, the ophthalmic imaging apparatus 1 can display first correspondence information and second correspondence information. The first correspondence information indicates the correspondence between the scan line image SL1 and the first moving image G1, and the second correspondence information indicates the correspondence between the scan line image SL2 and the second moving image G2. In the present example, display colors are used as the first correspondence information and the second correspondence information. More specifically, the display controller 2112 displays the scan line image SL1 and the rim of the first moving image G1 (i.e., the rim of the first moving image display area 301) in a first color, and displays the scan line image SL2 and the rim of the second moving image G2 (i.e., the rim of the second moving image display area 302) in a second color. Here, the first color and the second color are different from one another.

Further, the ophthalmic imaging apparatus 1 can display third correspondence information and fourth correspondence information. The third correspondence information indicates the correspondence between the scan position where the scan line image SL1 is located and the scan position in the second moving image G. The fourth correspondence information indicates the correspondence between the scan position where the scan line image SL2 is located and the scan position in the first moving image G1. In the second moving image G2, a scan position designation line 304 is displayed. The scan position designation line 304 indicates the position corresponding to the scan position where the scan line image SL1 is located. In the first moving image G1, a scan position designation line 305. The scan position designation line 305 indicates the position corresponding to the scan position where the scan line image SL2 is located. In the present example, display colors are used as the third correspondence information and the fourth correspondence information. More specifically, the display controller 2112 displays the scan line image SL1 and the scan position designation line 304 in the first moving image G1 in a first color, and displays the scan line image SL2 and the scan position designation line 305 in the second moving image G2 in a second color different from the first color. As the third correspondence information and the fourth correspondence information, the display forms of lines (e.g., solid line, wavy line, one dot chain line, line thickness, etc.) may be used.

A marker 306 indicating the focal position of the measurement light LS is provided on the left side of the first moving image display area 301. The focal position of the measurement light LS corresponds to the position of the focusing lens 43. The focusing lens 43 is moved by the OCT focus driver 43A. The display controller 2112 displays the marker 306 based on the current position of the focusing lens 43 (that is, based on the control state of the OCT focus driver 43A). The focal position changes in the z direction, and the direction along the left side of the first moving image display area 301 (i.e., the vertical direction) corresponds to the z direction. In this manner, the position of the marker 306 varies along the left side.

Further, the user can move the marker 306. The operation for this is performed by a touch operation of touching a desired position when the display unit 241 is a touch panel. If the display unit 241 is not a touch panel, the user operates the operation unit 242. This operation is, for example, an operation of clicking a desired position or an operation of dragging the marker 306. When the marker 306 is moved, the main controller 211 controls the OCT focus driver 43A based on the position of the marker 306 after the movement, so that the focusing lens 43 is moved to the position corresponding to the position of the marker 306 after the movement.

Note that the areas provided on the display screen 300 are not limited to those shown in FIG. 10. As a typical example, the display screen 300 may be provided with an area in which information related to the subject and/or the subject's eye E is displayed, an area in which an image of the anterior segment of the subject's eye E is displayed (referred to as an anterior segment image display area), various kinds of software keys, or the like.

An example related to the display of the anterior segment image and the accompanying process will be described. The ophthalmic imaging apparatus according to the present example includes a pair of video cameras for acquiring images of the anterior segment of the subject's eye E. The pair of video cameras takes images of the anterior segment simultaneously from different directions. The display controller 2112 displays the image area of the upper half of the image (referred to as an upper half area) obtained by the first video camera and the image area of the lower half of the image (referred to as a lower half area) obtained by the second video camera in the anterior segment image display area in such a manner that the upper half area and the lower half area are arranged in the vertical direction. The controller 210 (or the data processor 230) analyzes the upper half area and the lower half area respectively to detect the images of a specific site such as the pupil or the iris (referred to as a specific site image). In addition, the controller 210 (or the data processor 230) calculates the displacement between the specific site image in the upper half area and the specific site image in the lower half area. Then, the controller 210 moves the optical system (e.g., the OCT optical system, the fundus camera optical system) so as to eliminate the calculated displacement. With such processes, alignment of the optical system with respect to the subject's eye E can be performed. Furthermore, by repeatedly performing the above-described processing in real time based on frames sequentially acquired by the pair of video cameras, the ophthalmic imaging apparatus can perform tracking that makes the optical system to follow the movement of the subject's eye E during OCT measurement, photography, observation of the fundus Ef.

Other Operation Examples

Other operation examples that can be performed according to the present embodiment will be described.

In the present embodiment, the case has been described in which when a request to move the scan pattern image beyond the scannable area is performed by using the operation unit 242, the display position of the scan pattern image is controlled. However, the control may include other than the control of the display position. For example, the measurement controller 2111 may move the scannble range in the requested movement direction. In this case, the measurement controller 2111 moves the scan position by the optical scanner 42 by a predetermined movement amount (or a designated movement amount) in a direction corresponding to the requested movement direction. With such control, even when the movement is beyond the scannable area, it is possible to observe the site of interest at the position after the requested movement.

Further, for example, the measurement controller 2111 may change the projection position of the fixation target by the LCD 39 so that the scannable area is moved in the requested movement direction. In this case, the measurement controller 2111 moves the display position of the fixation target on the screen of the LCD 39 by a predetermined movement amount (or the designated movement amount) in the direction corresponding to the requested movement direction to change the projection position of the fixation target. With such control, even when the site of interest is located outside the scannable area, it is possible to observe the site of interest in the position after the requested movement.

Although the above example has described the case where the cross scan is applied, any scan pattern in which two or more scan areas intersect one another, like the radial scan, can also be applied.

[Actions and Effects]

Several actions and effects of the ophthalmic imaging apparatus according to the present embodiment will be described.

The ophthalmic imaging apparatus according to the embodiment acquires a cross sectional image by scanning the subject's eye using OCT. Further, the ophthalmic imaging apparatus includes a measurement unit (for example, the fundus camera unit 2 and the OCT unit 100), an imaging unit (the CCD image sensor 35 or the CCD image sensor 38; an imaging unit may further include an optical system for generating fundus reflection light detected by the CCD image sensor 35 or the CCD image sensor 38), a display controller (for example, the display controller 2112), an operation unit (for example, the operation unit 242), and a measurement controller (for example, the measurement controller 2111).

The measurement unit is configured to perform OCT. The imaging unit is configured to acquire a moving image of the subject's eye E. The display controller is configured to control a display device (for example, the display unit 241) to display the moving image acquired by the imaging unit, and two or more scan pattern images corresponding to two or more scan lines representing a scan position and a scan direction in the moving image and arranged such that at least two of the two or more scan pattern images intersect one another. The operation unit is used to change the relative position between the two or more scan pattern images. The measurement controller is configured to control the measurement unit to perform optical coherence tomography based on the two or more scan lines corresponding to the two or more scan pattern images after the relative position have been changed.

With such a configuration, the ophthalmic imaging apparatus displays, on the display device, a scan pattern that has two or more scan pattern images arranged such that at least two of the two or more scan pattern images intersect one another. In addition, the relative position between the two or more scan pattern images can be changed by using the operation unit. As a result, the degree of freedom of the movement of the intersection area of the two or more scan pattern images can be improved and the degree of freedom of scanning can be improved.

In addition, the operation unit may be used for a first movement operation for moving any of the two or more scan pattern images. Furthermore, the display controller may change the display position of the moved scan pattern image according to the first movement operation.

According to such a configuration, it is possible to move the intersection area of the scan pattern images to a desired position by moving any of the two or more scan pattern images while confirming the display position of the scan pattern images displayed on the display device.

In addition, the operation unit may be used for a second movement operation for integrally moving at least part of the two or more scan pattern images. Furthermore, the display controller may change the display position of the at least part of the two or more scan pattern images according to the second movement operation.

According to such a configuration, it is possible to move the intersection area of the scan pattern images to a desired position by integrally moving at least part of the two or more scan pattern images while confirming the display position of the scan pattern image displayed on the display device.

The second movement operation may include an operation of dragging an intersection area where at least two of the two or more scan pattern images intersect one another.

According to such a configuration, by performing the drag operation on the intersection area of the two or more scan pattern images while confirming the display position of the scan pattern image displayed on the display device, it is possible to move the intersection area of the scan pattern images to a desired position, and to easily observe the site of interest.

In addition, the second movement operation may include an operation of dragging a position in the moving image different from the positions of the two or more scan pattern images.

According to such a configuration, by performing the drag operation on a position in the moving image different from the two or more scan pattern images while confirming the display position of the scan pattern image displayed on the display device, it is possible to move the intersection area of the scan pattern images to a desired position, and to easily observe the site of interest.

The measurement unit may perform OCT within a predetermined scannable area, and the display controller may be capable of changing the display positions of the two or more scan pattern images within a display area corresponding to the scannable area.

According to such a configuration, the display positions of the scan pattern images can be changed within the display area corresponding to the scannable area displayed on the display device. Therefore, it is possible to prevent the situation where OCT measurement cannot be performed, and to easily observe the site of interest.

In addition, the display controller may control the display device to display an image representing the scannable area over the moving image.

According to such a configuration, it is possible to change the display positions of the scan pattern images while confirming the display area corresponding to the scannable area displayed on the display device. Therefore, the user can easily observe the site of interest within the area to which the OCT measurement is applicable.

When a request to move the scan pattern image beyond the scannable area by the first movement amount in the first movement direction is made by using the operation unit, the display controller may change the display position of the scan pattern image that has come into contact with the edge of the scannable area by the first movement amount in the second movement direction opposite to the first movement direction.

According to such a configuration, even when a request to move the scan pattern beyond the scannable area is made, it is possible to place the intersection area at an arbitrary position within the scannable area and to perform scanning of the site of interest without having to reduce the size (i.e., the dimension) of the scan area.

When a request to move a scan pattern image beyond the scannable area is made by using the operation unit, the display controller may stop the movement of the display position of at least the scan pattern image that has come into contact with the edge of the scannable area at this contact position.

According to such a configuration, even when a request to move the scan pattern beyond the scannable area is made, it is possible to place the intersection area at an arbitrary position within the scannable area and to perform scanning of the site of interest without having to reduce the area of the scan area.

When a request to move a scan pattern image beyond the scannable area is made by using the operation unit, the measurement controller may move the scannable area in the direction of the movement requested.

According to such a configuration, it is possible to observe the site of interest at the position after the requested movement, even outside the scannable area.

The ophthalmic imaging apparatus may include a fixation target projection unit (for example, the LCD 39) configured to project a fixation target on the subject's eye. In addition, when a request to move a scan pattern image beyond the scannable area is made by using the operation unit, the measurement controller may control the fixation target projection unit to change the projection position of the fixation target so that the scannable area is moved in the direction of the movement requested.

According to such a configuration, it is possible to observe the site of interest at the position after the requested movement, even outside the scannable area.

Further, the operation unit may be used for a size changing operation to change the size of at least part of the two or more scan pattern images, and the display controller may change the display size of the at least part of the two or more scan pattern images according to the size changing operation.

According to such a configuration, it becomes possible to change the size of the scan pattern according to the site of interest. As a result, the user can easily observe the desired site of interest based on a scan pattern of a suitable size within the scannable area.

At least part of the two or more scan pattern images may include two or more scan lines. The operation unit may be used for an operation for changing the relative position between the two or more scan lines. The measurement controller may control the measurement unit to perform OCT based on the two or more scan lines whose relative position have been changed.

According to such a configuration, it is possible to freely change the arrangement density of the scan lines, and the user can perform detailed observation according to the desired site of interest.

The configurations described above are mere examples for embodying or carrying out the present invention, and therefore susceptible to several modifications and variations (omission, substitution, addition, etc.), all coming within the scope of the invention. The configuration to be employed is selected according to the purpose, for example. In addition, depending on the configuration to be employed, actions and effects obvious to those skilled in the art and the actions and effects described in this specification can be achieved.

The invention claimed is:

1. An ophthalmic imaging apparatus that scans a subject's eye with optical coherence tomography to acquire a cross sectional image comprising:
   a first sensor configured to perform optical coherence tomography within a predetermined scannable area;
   a second sensor configured to acquire a moving image of the subject's eye;
   a processor programmed to perform as a display controller that controls a display device to display the moving image acquired by the second sensor, and two or more scan pattern images corresponding to two or more scan lines representing scan positions and scan directions in the moving image and arranged such that at least two of the two or more scan pattern images intersect one another; and
   an input device configured for changing a relative position between the two or more scan pattern images; wherein
   the processor is further programmed to perform as a measurement controller that controls the first sensor to perform the optical coherence tomography based on the two or more scan lines corresponding to the two or more scan pattern images after the relative position have been changed, and
   when a request to move a scan pattern image beyond the scannable area is made by using the input device, the measurement controller moves the scannable area in a movement direction requested.

2. The ophthalmic imaging apparatus of claim 1, wherein the input device is used for a first movement operation to move any of the two or more scan pattern images, and
   the display controller changes a display position of a moved scan pattern image according to the first movement operation.

3. The ophthalmic imaging apparatus of claim 1, wherein the input device is used for a second movement operation to integrally move at least part of the two or more scan pattern images, and
   the display controller changes a display position of the at least part of the two or more scan pattern images according to the second movement operation.

4. The ophthalmic imaging apparatus of claim 3, wherein the second movement operation comprises an operation of dragging an intersection area where the at least two of the two or more scan pattern images intersect one another.

5. The ophthalmic imaging apparatus of claim 3, wherein the second movement operation comprises an operation of dragging a position in the moving image different from the two or more scan pattern images.

6. The ophthalmic imaging apparatus of claim 1, wherein the display controller is capable of changing display positions of the two or more scan pattern images within a display area corresponding to the scannable area.

7. The ophthalmic imaging apparatus of claim 6, wherein the display controller displays an image representing the scannable area over the moving image.

8. The ophthalmic imaging apparatus of claim 6, wherein when a request to move a scan pattern image beyond the scannable area by a first movement amount in a first movement direction is made by using the input device, the display controller changes a display position of a scan pattern image that has come into contact with an edge of the scannable area by the first movement amount in a second movement direction opposite to the first movement direction.

9. The ophthalmic imaging apparatus of claim 6, wherein when a request to move a scan pattern image beyond the scannable area is made by using the input device, the display controller stops movement of a display position of at least a scan pattern image that has come into contact with an edge of the scannable area at a contact position.

10. An ophthalmic imaging apparatus that scans a subject's eye with optical coherence tomography to acquire a cross sectional image comprising:
    a first sensor configured to perform optical coherence tomography within a predetermined scannable area;
    a second sensor configured to acquire a moving image of the subject's eye;
    a processor programmed to perform as a display controller that controls a display device to display the moving image acquired by the second sensor, and two or more scan pattern images corresponding to two or more scan lines representing scan positions and scan directions in the moving image and arranged such that at least two of the two or more scan pattern images intersect one another;
    an input device configured for changing a relative position between the two or more scan pattern images;
    the processor is further programmed to perform as a measurement controller that controls the first sensor to perform the optical coherence tomography based on the two or more scan lines corresponding to the two or more scan pattern images after the relative position have been changed; and
    a fixation target projector configured to project a fixation target onto the subject's eye, wherein
    when a request to move a scan pattern image beyond the scannable area is made by using the input device, the measurement controller controls the fixation target projector to change a projection position of the fixation target so that the scannable area is moved in a movement direction requested.

11. The ophthalmic imaging apparatus of claim 1, wherein the input device is used for a size changing operation to change a size of at least part of the two or more scan pattern images, and
    the display controller changes a display size of the at least part of the two or more scan pattern images according to the size changing operation.

12. The ophthalmic imaging apparatus of claim 1, wherein
    at least part of the two or more scan pattern images comprises two or more scan lines,
    the input device is used for an operation to change the relative position between the two or more scan lines, and
    the measurement controller controls the first sensor to perform h optical coherence tomography based on the two or more scan lines whose relative position have been changed.

13. The ophthalmic imaging apparatus of claim 10, wherein
    the input device is used for a first movement operation to move any of the two or more scan pattern images, and
    the display controller changes a display position of a moved scan pattern image according to the first movement operation.

14. The ophthalmic imaging apparatus of claim 10, wherein
    the input device is used for a second movement operation to integrally move at least part of the two or more scan pattern images, and
    the display controller changes a display position of the at least part of the two or more scan pattern images according to the second movement operation.

15. The ophthalmic imaging apparatus of claim 14, wherein the second movement operation comprises an operation of dragging an intersection area where the at least two of the two or more scan pattern images intersect one another.

16. The ophthalmic imaging apparatus of claim 14, wherein the second movement operation comprises an operation of dragging a position in the moving image different from the two or more scan pattern images.

17. The ophthalmic imaging apparatus of claim 10, wherein
the display controller is capable of changing display positions of the two or more scan pattern images within a display area corresponding to the scannable area.

18. The ophthalmic imaging apparatus of claim 17, wherein the display controller displays an image representing the scannable area over the moving image.

19. The ophthalmic imaging apparatus of claim 17, wherein when a request to move a scan pattern image beyond the scannable area by a first movement amount in a first movement direction is made by using the input device, the display controller changes a display position of a scan pattern image that has come into contact with an edge of the scannable area by the first movement amount in a second movement direction opposite to the first movement direction.

20. The ophthalmic imaging apparatus of claim 17, wherein when a request to move a scan pattern image beyond the scannable area is made by using the input device, the display controller stops movement of a display position of at least a scan pattern image that has come into contact with an edge of the scannable area at a contact position.

21. The ophthalmic imaging apparatus of claim 10, wherein
the input device is used for a size changing operation to change a size of at least part of the two or more scan pattern images, and
the display controller changes a display size of the at least part of the two or more scan pattern images according to the size changing operation.

22. The ophthalmic imaging apparatus of claim 10, wherein
at least part of the two or more scan pattern images comprises two or more scan lines,
the input device is used for an operation to change the relative position between the two or more scan lines, and
the measurement controller controls the first sensor to perform the optical coherence tomography based on the two or more scan lines whose relative position have been changed.

\* \* \* \* \*